(12) United States Patent
Ma et al.

(10) Patent No.: US 10,494,619 B2
(45) Date of Patent: Dec. 3, 2019

(54) HIGH ISOMEROHYDROLASE ACTIVITY MUTANTS OF HUMAN RPE65

(71) Applicant: The Board of Regents of the University of Oklahoma, Norman, OK (US)

(72) Inventors: Jian-Xing Ma, Edmond, OK (US); Yusuke Takahashi, Oklahoma City, OK (US); Gennadiy Moiseyev, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 151 days.

(21) Appl. No.: 15/500,837

(22) PCT Filed: Jul. 27, 2015

(86) PCT No.: PCT/US2015/042263
§ 371 (c)(1),
(2) Date: Jan. 31, 2017

(87) PCT Pub. No.: WO2016/018816
PCT Pub. Date: Feb. 4, 2016

(65) Prior Publication Data
US 2017/0226490 A1 Aug. 10, 2017

Related U.S. Application Data

(60) Provisional application No. 62/031,472, filed on Jul. 31, 2014.

(51) Int. Cl.
*A61K 48/00* (2006.01)
*C12N 15/86* (2006.01)
(Continued)

(52) U.S. Cl.
CPC .............. *C12N 9/18* (2013.01); *C12N 7/00* (2013.01); *C12N 15/86* (2013.01);
(Continued)

(58) Field of Classification Search
CPC ...... A61K 48/00; A61K 48/005; C12N 15/86; C12N 15/861; C12N 15/8645; C12N 2710/10343; C12Y 301/01064
See application file for complete search history.

(56) References Cited

U.S. PATENT DOCUMENTS 4,394,448 A 7/1983 Szoka, Jr. et al.
5,139,941 A 8/1992 Muzyczka et al.
(Continued)

FOREIGN PATENT DOCUMENTS

EP 0820773 A1 1/1998
WO 1996018418 A1 6/1996
(Continued)

OTHER PUBLICATIONS

Moiseyev et al, J. Biol. Chem. 283(13): 8110-8117, 2008.*
(Continued)

*Primary Examiner* — Kevin K Hill
(74) *Attorney, Agent, or Firm* — Hall Estill Law Firm

(57) ABSTRACT

Mutant mammalian RPE65 proteins and portions thereof, and nucleic acids encoding the mutants, for use in treating a condition related to retinal degeneration in a subject, the mutant mammalian RPE65 proteins or portions thereof having isomerohydrolase activity. A gene therapy method of treating a condition related to retinal degeneration in a mammalian subject in need of such treatment, comprising administering to the subject a therapeutically-effective amount of a vector comprising a nucleic acid encoding a mutant mammalian RPE65 protein or a portion thereof. A method of treating a condition related to retinal degeneration in a subject in need of such treatment, comprising administering to the subject a therapeutically-effective amount of at least one of a mutant mammalian RPE65 protein or a portion thereof.

23 Claims, 26 Drawing Sheets

Specification includes a Sequence Listing.

(51) Int. Cl.
*C12N 9/18* (2006.01)
*C12N 7/00* (2006.01)

(52) U.S. Cl.
CPC ...... *C12Y 301/01064* (2013.01); *A61K 48/00* (2013.01); *C12N 2710/10343* (2013.01)

(56) References Cited

U.S. PATENT DOCUMENTS

| | | |
|---|---|---|
| 5,288,641 A | 2/1994 | Roizman |
| 5,399,346 A | 3/1995 | Anderson et al. |
| 5,436,146 A | 7/1995 | Shenk et al. |
| 5,622,856 A | 4/1997 | Natsoulis |
| 5,665,577 A | 9/1997 | Sodroski et al. |
| 5,672,510 A | 9/1997 | Eglitis et al. |
| 5,676,954 A | 10/1997 | Brigham |
| 5,707,865 A | 1/1998 | Kohn et al. |
| 5,817,491 A | 10/1998 | Yee et al. |
| 5,935,935 A | 8/1999 | Connelly et al. |
| 5,994,136 A | 11/1999 | Naldini et al. |
| 6,013,516 A | 1/2000 | Verma et al. |
| 6,217,912 B1 | 4/2001 | Park et al. |
| 7,514,098 B2 | 4/2009 | Bednarski et al. |
| 8,147,823 B2 * | 4/2012 | Acland ............ A61K 31/70 424/93.2 |
| 8,323,618 B2 | 12/2012 | Bikram |
| 8,785,413 B2 | 7/2014 | Blanks et al. |
| 2003/0003582 A1 * | 1/2003 | Wakefield ........ A61K 48/0058 435/456 |

FOREIGN PATENT DOCUMENTS

| | | |
|---|---|---|
| WO | 9848097 | 10/1998 |
| WO | 2000015822 A1 | 3/2000 |
| WO | WO 12/145601 | * 10/2012 |

OTHER PUBLICATIONS

Mayer et al, BMC Bioinformatics 6:284, 9 pages, 2005.*
Gerth and Lutz, Biochem. Biophys. Res. Comm. 354: 802-807, 2007.*
PCT/US2015/042263; International Search Report and Written Opinion; dated Dec. 31, 2015; 17 pages.
Gennadiy, et al.; "RPE65 from Cone-dominated Chicken Is a More Efficient Isomeronydrolase Compared with That from Rod-dominant Species"; Journal of Biological Chemistry; Mar. 28, 2008; pp. 8110-8117; 9 pages total; vol. 283, No. 13.
Cideciyan, et al.; "Human gene therapy for RPE65 isomerase deficiency activates the retinoid cycle of vision but with slow rod kinetics"; PNAS; Sep. 30, 2008; pp. 15112-15117; 11 pages total; vol. 105, No. 39.
"Atlas of protein sequence and structure" (1972) 5, 120-130.
Shenk, et al.; "Genetic Analysis of Adenoviruses"; Current Topics in Microbiology and Immunology (1984) 111, 1-39.
Berkner, et al.; "Development of adenovirus vectors for the expression of heterologous genes"; Biotechniques (1988) 6, 616-629.
Myers, E.W., et al.; "Optimal alignments in linear space"; Cabios (1988) 4:1, 11-17.
Pearson, W.R., et al.; "Improved tools for biological sequence comparison"; Proc. Natl. Acad. Sci. USA (Apr. 1988) 85, pp. 2444-2448.
Altschul, S.F., et al.; "Basic Local Alignment Search Tool"; J. Mol. Biol. (1990) 215, 403-410.
Karlin, S., et al.; "Methods for assessing the statistical significance of molecular sequence features by using general scoring schemes"; Proc. Natl. Acad. Sci. USA (Mar. 1990) 87, 2264-2268.
Gomez-Foix, A.M., et al.; "Adenovirus-mediated Transfer of the Muscle Glycogen Phosphorylase Gene into Hepatocytes Confers Altered Regulation of Glycogen Metabolism"; The Journal of Biological Chemistry (Dec. 1992) 267:35, 25129-25134.
Gish, W., et al.; "Identification of protein coding regions by database similarity search"; Nature Genetics (Mar. 1993) 3, 266-272.
Karlin, S., et al.; "Applications and statistics for multiple high-scoring segments in molecular sequences"; Proc. Natl. Acad. Sci. USA (Jun. 1993) 90, 5873-5877.
Mulligan, R.C.; "The Basic Science of Gene Therapy"; Science (May 14, 1993) 260, 926-932.
Baque, S., et al.; "Adenovirus-mediated delivery into myocytes of muscle glycogen phosphorylase, the enzyme deficient in patients with glycogen-storage disease type V"; Biochem. J. (1994) 304, 1009-1014.
Bennett, J., et al.; "Adenovirus Vector-Mediated in Vivo Gene Transfer Into Adult Murine Retina"; Investigative Ophthalmology & Visual Science (Apr. 1994) 35:5, 2535-2542.
Hitt, M., et al.; "Techniques for Human Adenovirus Vector Construction and Characterization"; Methods in Molecular Genetics (1995) 7, 13-30.
Altschul, S.F., et al.; "Local Alignment Statistics"; Multiple Alignment and Phylogenetic Trees; Methods in Enzymology (1996) 266, 460-480.
Chartier, C., et al.; "Efficient Generation of Recombinant Adenovirus Vectors by Homologous Recombination in *Escherichia coli*"; Journal of Virology (Jul. 1996) 70:7, 4805-4810.
Miyoshi, H., et al.; "Stable and efficient gene transfer into the retina using an HIV-based lentiviral vector"; Proc. Natl. Acad. Sci. USA (Sep. 1997) 94, 10319-10323.
He, T., et al.; "A simplified system for generating recombinant adenoviruses"; Proc. Natl. Acad. Sci. USA (Mar. 1998) 95, 2509-2514.
Manes, G., et al.; "Rat messenger RNA for the retinal pigment epithelium-specific protein RPE65 gradually accumulates in two weeks from late embryonic days"; FEBS 19849 (1998) 423, 133-137.
Morsy, M.A., et al.; "Expanded-capacity adenoviral vectors—the helper-dependent vectors"; Molecular Medicine Today (Jan. 1999) 18-24.
Auricchio, A., et al.; "Exchange of surface proteins impacts on viral vector cellular specificity and transduction characteristics: the retina as a model"; Human Molecular Genetics (2001) 10:26, 3075-3081.
Ma, J., et al.; "Expression, Purification, and MALDI Analysis of RPE65"; Investigative Ophthalmology & Visual Science (Jun. 2001) 42:7, 1429-1435.
Narfstrom, K., et al.; "Functional and Structural Recovery of the Retina after Gene Therapy in the RPE65 Null Mutation Dog"; Investigative Ophthalmology & Visual Science (Apr. 2003) 44:4, 1663-1672.
Weber, M., et al.; "Recombinant Adeno-associated Virus Serotype 4 Mediates Unique and Exclusive Long-Term Transduction of Retinal Pigmented Epithelium in Rat, Dog, and Nonhuman Primate after Subretinal Delivery"; Molecular Therapy (Jun. 2003) 7:6, 774-781.
Kachi, S., et al.; "Nonviral ocular gene transfer"; Gene Therapy (2005) 12, 843-851.
Moiseyev, G., et al.; "RPE65 is the isomerohydrolase in the retinoid visual cycle"; PNAS (Aug. 30, 2005) 102:35, 12413-12418.
Bemelmans, A., et al.; "Lentiviral Gene Transfer of RPE65 Rescues Survival and Function of Cones in a Mouse Model of Leber Congenital Amaurosis"; PLOS Medicine (Oct. 2006) 3:10, 1892-1903.
Farjo, R., et al.; "Efficient Non-Viral Ocular Gene Transfer with Compacted DNA Nanoparticles" PLOS One (Dec. 2006) 1, 1-8.
Yanez-Munoz, R.J., et al.; "Effective gene therapy with nonintegrating lentiviral vectors"; Nature Medicine (Mar. 2006) 12:3, 348-353.
Yokoi, K., et al.; "Ocular Gene Transfer with Self-Complementary AAV Vectors"; IOVS (Jul. 2007) 48:7, 3324-3328.
Johnson, C.J., et al.; "Technical Brief: Subretinal injection and electroporation into adult mouse eyes"; Molecular Vision (2008) 14, 2211-2226.
Moiseyev, G., et al.; "RPE65 from Cone-dominant Chicken Is a More Efficient Isomerohydrolase Compared with That from Rod-dominant Species"; Journal of Biological Chemistry (Mar. 28, 2008) 283:13, 8110-8117.

(56) References Cited

OTHER PUBLICATIONS

Pang, J., et al.; "Comparative analysis of in vivo and in vitro AAV vector transduction in the neonatal mouse retina: Effects of serotype and site of administration"; Vision Research (2008) 48, 377-385.

Zhang, S., et al.; "Distinctive Gene Transduction Efficiencies of Commonly Used Viral Vectors in the Retina"; Current Eye Research (2008) 33, 81-90.

Takahashi, Y., et al.; "Identification of Key Residues Enhancing Isomerohydrolase Activity of Human RPE65 for More Efficient Gene Therapy"; ARVO Annual Meeting Abstract (Apr. 2014) 55:13, 2 pages (Abstract Only).

Singapore Application No. 11201700724P; "Search Report and Written Opinion"; IPOS (dated Mar. 16, 2018) 8 pages.

Manes, et al.; "Retinal pigment epithelium-specific protein [Rattus norvegicus]"; FEBS Lett. 423(2), 133-137 (1998) Abstract only.

Mayer, et al.; "Linking enzyme sequence to function using conserved property difference locator to identify and annotate positions likely to control specific functionality"; BioMed Central; BMC Bioinformatics; 6:284 (2005) 1-9.

Gerth, et al.; "Mutagenesis of non-conserved active stie residues improves the activity and narrows the specificity of human thymidine kinage 2"; Biochemical and Biophysical Research Communications 354 (2007) 802-807.

"Clean Claims" filed in SG11201700724P; Jul. 2017; 8 pages.

Ja Kemp; "Letter Reporting Extended Search Report"; EP15826829.2; dated Jan. 12, 2018; 3 pages.

IPOS; "Search Report and Written Opinion"; SG11201700724P; dated Mar. 16, 2018; 8 pages.

Ja Kemp; "Letter Reporting Written Opinion"; SG11201700724P; dated May 10, 2018; 3 pages.

\* cited by examiner

```
                  10         20         30         40         50         60         70         80
                   |          |          |          |          |          |          |          |
human    MSIQVEHPAGGYKKLFETVEELSSPLTAHVTGRIPIWLTGSLLRCGPGLFEVGSEPFYHLFDGQALLHKFDFKEGHVTYH
chicken  .YS......................V..................T..R............A.................

90        100        110        120        130        140        150        160
                   |          |          |          |          |          |          |          |
human    RRFIRTDAYVRAMTEKRIVITEFGTCAFPDPCKNIFSRFFSYFRGVEVTDNALVNVYPVGEDYYACTETNFITKINPETL
chicken  ...V...............................Y.Y.............K..........................D..

170        180        190        200        210        220        230        240
                   |          |          |          |          |          |          |          |
human    ETIKQVDLCNYVSVNGATAHPHIENDGTVYNIGNCFGKNFSIAYNIVKIPPLQADKEDPISKSEIVVQFPCSDRFKPSYV
chicken  ........K..........V...................L...IR..............MN..V...............

250        260        270        280        290        300        310        320
                   |          |          |          |          |          |          |          |
human    HSFGLTPNYIVFVETPVKINLFKFLSSWSLWGANYMDCFESNETMGVWLHIADKKRKKYLNNKYRTSPFNLFHHINTYED
chicken  ....................L............................V.E..KGRL..I......A......F...

330        340        350        360        370        380        390        400
                   |          |          |          |          |          |          |          |
human    NGFLIVDLCCWKGFEFVYNYLYLANLRENWEEVKKNARKAPQPEVRRYVLPLNIDKADTGKNLVTLPNTTATAILCSDET
chicken  ........T..............................A..D...Q.E.......A......R......Y.....T.R....

410        420        430        440        450        460        470        480
                   |          |          |          |          |          |          |          |
human    IWLEPEVLFSGPRQAFEFPQINYQKYCGKPYTYAYGLGLNHFVPDRLCKLNVKTKETWVQEPDSYPSEPIFVSHPDALE
chicken  V........I...H...........K..G.......T..........................................

490        500        510        520        530
                   |          |          |          |          |
human    EDDGVVLSVVVSPGAGQKPAYLLILNAKDLSEVARAEVEINIPVTFHGLFKKS
chicken  .....I.I...S.P..............M......V...........RA
```

FIG.1

Human RPE65 protein (SEQ ID NO:1)
MSIQVEHPAGGYKKLFETVEELSSPLTAHVTGRIPLWLTGSLLRCGPGLFEVGSEPFYHLFDGQALLH
KFDFKEGHVTYHRRFIRTDAYVRAMTEKRIVITEFGTCAFPDPCKNIFSRFFSYFRGVEVTDNALVNV
YPVGEDYYACTETNFITKINPETLETIKQVDLCNYVSVNGATAHPHIENDGTVYNIGNCFGKNFSIAY
NIVKIPPLQADKEDPISKSEIVVQFPCSDRFKPSYVHSFGLTPNYIVFVETPVKINLFKFLSSWSLWG
ANYMDCFESNETMGVWLHIADKKRKKYLNNKYRTSPFNLFHHINTYEDNGFLIVDLCCWKGFEFVYNY
LYLANLRENWEEVKKNARKAPQPEVRRYVLPLNIDKADTGKNLVTLPNTTATAILCSDETIWLEPEVL
FSGPRQAFEFPQINYQKYCGKPYTYAYGLGLNHFVPDRLCKLNVKTKETWVWQEPDSYPSEPIFVSHP
DALEEDDGVVLSVVVSPGAGQKPAYLLILNAKDLSEVARAEVEINIPVTFHGLFKKS

FIG.2A

Human RPE65 nucleic acid (SEQ ID NO:2)
ATGTCTATCCAGGTTGAGCATCCTGCTGGTGGTTACAAGAAACTGTTTGAAACTGTGGAGGAACTGTC
CT
CGCCGCTCACAGCTCATGTAACAGGCAGGATCCCCCTCTGGCTCACCGGCAGTCTCCTTCGATGTGGG
CC
AGGACTCTTTGAAGTTGGATCTGAGCCATTTTACCACCTGTTTGATGGGCAAGCCCTCCTGCACAAGT
TT
GACTTTAAAGAAGGACATGTCACATACCACAGAAGGTTCATCCGCACTGATGCTTACGTACGGGCAAT
GA
CTGAGAAAGGATCGTCATAACAGAATTTGGCACCTGTGCTTTCCCAGATCCCTGCAAGAATATATTT
TC
CAGGTTTTTTTCTTACTTTCGAGGAGTAGAGGTTACTGACAATGCCCTTGTTAATGTCTACCCAGTGG
GG
GAAGATTACTACGCTTGCACAGAGACCAACTTTATTACAAAGATTAATCCAGAGACCTTGGAGACAAT
TA
AGCAGGTTGATCTTTGCAACTATGTCTCTGTCAATGGGGCCACTGCTCACCCCACATTGAAAATGAT
GG
AACCGTTTACAATATTGGTAATTGCTTTGGAAAAAATTTTTCAATTGCCTACAACATTGTAAAGATCC
CA
CCACTGCAAGCAGACAAGGAAGATCCAATAAGCAAGTCAGAGATCGTTGTACAATTCCCCTGCAGTGA
CC
GATTCAAGCCATCTTACGTTCATAGTTTTGGTCTGACTCCCAACTATATCGTTTTTGTGGAGACACCA
GT
CAAAATTAACCTGTTCAAGTTCCTTTCTTCATGGAGTCTTTGGGGAGCCAACTACATGGATTGTTTTG
AG
TCCAATGAAACCATGGGGGTTTGGCTTCATATTGCTGACAAAAAAGGAAAAAGTACCTCAATAATAA
AT
ACAGAACTTCTCCTTTCAACCTCTTCCATCACATCAACACCTATGAAGACAATGGGTTTCTGATTGTG
GA
TCTCTGCTGCTGGAAAGGATTTGAGTTTGTTTATAATTACTTATATTTAGCCAATTTACGTGAGAACT
GG
GAAGAGGTGAAAAAAAATGCCAGAAAGGCTCCCCAACCTGAAGTTAGGAGATATGTACTTCCTTTGAA
TA
TTGACAAGGCTGACACAGGCAAGAATTTAGTCACGCTCCCCAATACAACTGCCACTGCAATTCTGTGC
AG
TGACGAGACTATCTGGCTGGAGCCTGAAGTTCTCTTTTCAGGGCCTCGTCAAGCATTTGAGTTTCCTC
AA
ATCAATTACCAGAAGTATTGTGGGAAACCTTACACATATGCGTATGGACTTGGCTTGAATCACTTTGT
TC
CAGATAGGCTCTGTAAGCTGAATGTCAAAACTAAAGAAACTTGGGTTTGGCAAGAGCCTGATTCATAC
CC
ATCAGAACCCATCTTTGTTTCTCACCCAGATGCCTTGGAAGAAGATGATGGTGTAGTTCTGAGTGTGG
TG
GTGAGCCCAGGAGCAGGACAAAAGCCTGCTTATCTCCTGATTCTGAATGCCAAGGACTTAAGTGAAGT
TG
CCCGGGCTGAAGTGGAGATTAACATCCCTGTCACCTTTCATGGACTGTTCAAAAAATCTTGA

FIG.2B

```
Chicken RPE65 protein (SEQ ID NO:3)
MYSQVEHPAGGYKKLFETVEELSSPVTAHVTGRIPTWLRGSLLRCGPGLFEVGAEPFYHLFDGQALLH
KFDFKEGHVTYHRRFVRTDAYVRAMTEKRIVITEFGTYAYPDPCKNIFSRFFSYFKGVEVTDNALVNV
YPVGEDYYACTETNFITKINPDTLETIKQVDLCKYVSVNGATAHPHVENDGTVYNIGNCFGKNFSLAY
NIIRIPPLQADKEDPMNKSEVVVQFPCSDRFKPSYVHSFGLTPNYIVFVETPVKINLLKFLSSWSLWG
ANYMDCFESNETMGVWLHVAEKKKGRLLNIKYRTSAFNLFHHINTFEDNGFLIVDLCTWKGFEFVYNY
LYLANLRANWDEVKKQAEKAPQPEARRYVLPLRIDKADTGKNLVTLPYTTATATLRSDETVWLEPEVI
FSGPRHAFEFPQINYKKYGGKPYTYTYGLGLNHFVPDRLCKLNVKTKETWVWQEPDSYPSEPIFVSHP
DALEEDDGVVLSIVISPGSGPKPAYLLILNAKDMSEVARAEVEVNIPVTFHGLFKRA
```

FIG.2C

```
Chicken RPE65 nucleic acid (SEQ ID NO:4)
ATGTACAGCCAGGTGGAGCATCCCGCGGGAGGTTACAAGAAGCTCTTCGAGACAGTGGAGGAGCTGTC
CT
CACCCGTCACTGCTCACGTCACAGGCAGGATCCCCACCTGGCTCAGAGGCAGCCTCCTGCGATGTGGG
CC
TGGCCTCTTTGAAGTCGGGGCAGAGCCGTTCTACCACCTCTTCGATGGCCAGGCACTGCTGCACAAGT
TT
GACTTCAAGGAGGGACATGTCACCTACCACCGGAGGTTTGTTAGGACAGATGCTTATGTGCGAGCCAT
GA
CGGAGAAGAGGATTGTGATAACTGAATTTGGTACCTACGCCTACCCAGACCCGTGCAAGAACATTTTC
TC
CAGGTTTTTCTCCTACTTTAAAGGGGTGGAGGTCACCGATAACGCCCTCGTTAATGTCTACCCTGTTG
GT
GAGGACTACTACGCCTGTACGGAGACCAACTTTATAACCAAAATTAACCCAGACACTCTAGAGACAAT
TA
AGCAGGTGGATCTCTGCAAGTACGTCTCCGTCAATGGGGCCACAGCTCACCCCCACGTGGAGAACGAC
GG
CACAGTTTACAACATTGGCAACTGCTTTGGGAAAAATTTCTCGCTGGCCTACAACATCATACGGATTC
CT
CCACTCCAGGCAGACAAGGAGGACCCAATGAACAAGTCAGAGGTGGTGGTGCAGTTCCCTTGCAGTGA
CA
GATTTAAGCCCTCCTACGTGCACAGTTTTGGCCTGACCCCAAACTACATTGTATTTGTCGAAACCCCG
GT
GAAGATCAACCTCCTCAAGTTCCTCTCCTCCTGGAGCCTCTGGGGAGCCAACTACATGGACTGCTTTG
AG
TCCAACGAGACCATGGGGGTCTGGCTTCACGTGGCAGAGAAAAAGAAAGGGCGGCTCCTCAATATCAA
GT
ACCGGACCTCAGCCTTCAACCTCTTCCATCACATCAACACCTTCGAGGATAATGGGTTCCTCATTGTC
GA
CCTCTGCACATGGAAGGGATTCGAGTTCGTTTACAATTACCTCTACTTAGCCAACCTCCGAGCAAACT
GG
GATGAGGTAAAGAAGCAGGCTGAGAAGGCCCCCAGCCCGAAGCCCGCAGATACGTGCTGCCCCTCCG
CA
TCGACAAGGCTGACACAGGCAAAAACTTGGTCACCCTGCCCTACACGACAGCCACTGCGACGCTGCGC
AG
CGATGAGACCGTCTGGCTGGAGCCAGAAGTTATTTTCTCAGGGCCACGCCATGCCTTTGAATTTCCAC
AG
ATCAATTACAAGAAATACGGTGGGAAACCATATACATACACGTATGGGCTTGGACTGAATCACTTTGT
TC
CAGACAGGCTTTGCAAGCTGAATGTTAAAACAAAGGAGACCTGGGTGTGGCAGGAGCCAGATTCATAC
CC
ATCAGAGCCAATCTTCGTTTCCCATCCAGATGCTCTGGAGGAGGATGATGGGGTGGTGCTGAGCATTG
TG
ATCAGCCCTGGCTCAGGGCCGAAGCCTGCCTACCTCCTGATCCTGAATGCCAAGGACATGAGTGAAGT
GG
CCAGGGCAGAAGTGGAGGTGAACATCCCTGTGACTTTCCATGGACTCTTCAAAAGAGCATGA
```

FIG.2D crab-eating macaque RPE65 protein (SEQ ID NO:5)
MSIQVEHPAGGYKKLFETVEELSSPLTAHVTGRIPLWLTGSLLRCGPGLFEVGSEPFYHLFDGQALLHKF
DFKEGHVTYHRRFIRTDAYVRAMTEKRIVITEFGTCAFPDPCKNIFSRFFSYFRGVEVTDNALVNVYPVG
EDYYACTETNFITKINPETLETIKQVDLCNYVSVNGATAHPHIENDGTVYNIGNCFGKNFSIAYNIVKIP
PLQADKEDPISKSEIVVQFPCSDRFKPSYVHSFGLTPNYIVFVETPVKINLFKFLSSWSLWGANYMDCFE
SNETMGVWLHIADKKRKKYLNNKYRTSPFNLFHHINTYEDNGFLIVDLCCWKGFEFVYNYLYLANLRENW
EEVKKNARKAPQPEVRRYVLPLNIDKADTGKNLITLPNTTATAILCSDETIWLEPEVLFSGPRQAFEFPQ
INYQKYCGKPYTYAYGLGLNHFVPDRLCKLNVKTKETWVWQEPDSYPSEPIFVSHPDALEEDDGVVLSVV
VSPGAGQKPAYLLILNAKDLSEVARAEVEINIPVTFHGLFKKS

FIG.2E crab-eating macaque RPE65 nucleic acid (SEQ ID NO:6)
ATGTCTATCCAGGTCGAGCATCCTGCTGGTGGTTACAAGAAACTGTTTGAAACTGTGGAGGAACTGTCCT
CGCCGCTCACGGCTCATGTAACAGGCAGGATCCCCCTGTGGCTCACCGGCAGTCTCCTTCGATGTGGGCC
AGGACTCTTTGAAGTTGGATCTGAGCCATTTTACCACCTGTTTGATGGGCAAGCCCTCCTGCACAAGTTT
GACTTCAAAGAAGGACACGTCACATACCACAGAAGGTTCATCCGCACTGATGCTTACGTACGGGCAATGA
CTGAGAAAGGATCGTCATAACAGAATTTGGCACCTGTGCTTTCCCAGATCCCTGCAAGAATATATTTC
CAGGTTTTTTTCTTACTTTCGAGGAGTGGAGGTTACCGACAATGCCCTTGTTAATGTCTACCCAGTGGGG
GAAGATTACTACGCTTGCACAGAGACCAACTTTATTACAAAGATTAATCCAGAGACCTTGGAGACAATTA
AGCAGGTTGATCTTTGCAACTACGTCTCCGTCAATGGAGCCACTGCTCACCCCCACATTGAAAATGATGG
AACCGTTTACAATATTGGTAATTGCTTTGGAAAAAATTTTTCAATTGCCTACAACATTGTAAAGATCCCA
CCACTGCAAGCAGACAAGGAAGATCCAATAAGCAAGTCAGAGATCGTTGTACAATTCCCCTGCAGTGACC
GATTCAAGCCATCTTACGTTCATAGTTTTGGTCTGACTCCCAACTATATCGTTTTTGTGGAGACACCAGT
CAAAATTAACCTGTTCAAGTTCCTTTCTTCATGGAGTCTTTGGGGAGCCAACTACATGGATTGCTTTGAG
TCCAATGAAACCATGGGGGTTTGGCTTCATATTGCTGACAAAAAAAGGAAAAAGTACCTCAATAATAAAT
ACAGGACTTCTCCTTTCAACCTCTTCCATCACATCAACACCTATGAAGACAATGGGTTTCTGATTGTGGA
TCTCTGCTGCTGGAAAGGATTTGAGTTTGTTTATAATTACTTATATTTAGCCAATTTACGTGAGAACTGG
GAAGAAGTGAAAAAAAATGCCAGAAAGGCTCCCCAACCTGAAGTTAGGAGATACGTACTTCCTTTGAATA
TTGACAAGGCTGACACTGGCAAGAATTTAATCACGCTCCCCAATACAACTGCCACTGCAATTCTGTGCAG
TGACGAGACAATCTGGCTGGAGCCTGAGGTTCTCTTTTCAGGGCCTCGCCAAGCATTTGAGTTTCCTCAA
ATCAATTACCAGAAGTATTGTGGGAAACCTTACACATACGCGTATGGACTTGGCTTGAATCACTTTGTTC
CAGATAGGCTCTGTAAGCTGAATGTCAAAACTAAAGAAACTTGGGTTTGGCAAGAGCCTGATTCATACCC
ATCAGAACCCATCTTTGTTTCTCACCCAGATGCCTTGGAAGAAGATGATGGTGTAGTTCTGAGTGTGGTG
GTGAGCCCAGGAGCAGGACAAAAGCCTGCTTATCTCCTGATTCTGAATGCCAAGGACTTAAGTGAAGTTG
CCCGGGCTGAAGTGGAGATTAACATCCCTGTCACCTTTCATGGACTGTTCAAAAAATCTTGA

FIG.2F green monkey RPE65 protein (SEQ ID NO:7)
MSIQVEHPAGGYKKLFETVEELSSPLTAHVTGRIPLWLTGSLLRCGPGLFEVGSEPFYHLFDGQALLHKF
DFKEGHVTYHRRFIRTDAYVRAMTEKRIVITEFGTCAFPDPCKNIFSRFFSYFRGVEVTDNALVNVYPVG
EDYYACTETNFITKINPETLETIKQVDLCNYVSVNGATAHPHIENDGTVYNIGNCFGKNFSIAYNIVKIP
PLQADKEDPISKSEIVVQFPCSDRFKPSYVHSFGLTPNYIVFVETPVKINLFKFLSSWSLWGANYMDCFE
SNETMGVWLHIADKKRKKYLNNKYRTSPFNLFHHINTYEDNGFLIVDLCCWKGFEFVYNYLYLANLRENW
EEVKKNARKAPQPEVRRYVLPLNIDKADTGKNLITLPNTTATAILCSDETIWLEPEVLFSGPRQAFEFPQ
INYQKYCGKPYTYAYGLGLNHFVPDRLCKLNVKTKETWVWQEPDSYPSEPIFVSHPDALEEDDGVVLSVV
VSPGAGQKPAYLLILNAKDLSEVARAEVEINIPVTFHGLFKKS

FIG.2G green monkey RPE65 nucleic acid (SEQ ID NO:8)
ATGTCTATCCAGGTCGAGCATCCTGCTGGTGGTTACAAGAAACTGTTTGAAACTGTGGAGGAACTGTCCT
CGCCGCTCACAGCTCATGTAACAGGCAGGATCCCCCTGTGGCTCACCGGCAGTCTCCTTCGATGTGGGCC
AGGACTCTTTGAAGTTGGATCTGAGCCATTTTACCACCTGTTTGATGGGCAAGCCCTTCTGCACAAGTTT
GACTTTAAAGAAGGACACGTCACATACCACAGAAGGTTCATCCGCACTGATGCTTACGTACGGGCCATGA
CTGAGAAAAGGATCGTCATAACAGAATTTGGCACCTGTGCTTTCCCAGATCCCTGCAAGAATATATTTTC
CAGGTTTTTTTCTTACTTTCGAGGAGTGGAGGTTACCGACAATGCCCTTGTTAATGTCTACCCAGTGGGG
GAAGACTACTACGCTTGCACAGAGACCAACTTTATTACAAAGATTAATCCAGAGACCTTGGAGACAATTA
AGCAGGTTGATCTTTGCAACTACGTCTCCGTCAATGGAGCCACTGCTCACCCCCACATTGAAAATGATGG
AACCGTTTACAATATTGGTAATTGCTTTGGAAAAAATTTTTCAATTGCCTACAACATTGTAAAGATCCCA
CCACTGCAAGCAGACAAGGAAGATCCAATAAGCAAGTCAGAGATCGTTGTACAATTCCCCTGCAGTGACC
GATTCAAGCCATCTTACGTTCATAGTTTTGGTCTGACTCCCAACTATATCGTTTTTGTGGAGACACCAGT
CAAAATTAACCTGTTCAAGTTCCTTTCTTCATGGAGTCTTTGGGGAGCCAACTACATGGATTGCTTTGAG
TCCAATGAAACCATGGGGGTTTGGCTTCATATTGCTGACAAAAAAGGAAAAAGTACCTCAATAATAAAT
ACAGGACTTCTCCTTTCAACCTCTTCCATCACATCAACACCTATGAAGACAATGGGTTTCTGATTGTGGA
TCTCTGCTGCTGGAAAGGATTTGAGTTTGTTTATAATTACTTATATTTAGCCAATTTACGTGAGAACTGG
GAAGAGGTGAAAAAAAATGCCAGAAAGGCTCCCCAACCTGAAGTTAGGAGATATGTACTTCCTTTGAATA
TTGACAAGGCTGACACAGGCAAGAATTTAATCACGCTCCCCAATACAACTGCCACTGCAATTCTGTGCAG
TGACGAGACAATCTGGCTGGAGCCTGAGGTTCTCTTTTCAGGGCCTCGCCAAGCGTTTGAGTTTCCTCAA
ATCAATTACCAGAAGTATTGTGGGAAACCTTACACATACGCATATGGACTTGGCTTGAATCACTTTGTTC
CAGATAGGCTCTGTAAGCTGAATGTCAAAACTAAAGAAACTTGGGTTTGGCAAGAGCCTGATTCATACCC
ATCAGAACCCATCTTTGTTTCTCACCCAGATGCCTTGGAAGAAGATGATGGTGTAGTTCTGAGTGTGGTG
GTGAGCCCAGGAGCAGGACAAAAGCCTGCTTATCTCCTGATTCTGAATGCCAAGGACTTAAGTGAAGTTG
CCCGGGCTGAAGTGGAGATTAACATCCCTGTCACCTTTCACGGACTGTTCAAAAAATCTTGA

FIG.2H

Bovine RPE65 protein (SEQ ID NO:9)
MSSQVEHPAGGYKKLFETVEELSSPLTAHVTGRIPLWLTGSLLRCGPGLFEVGSEPFYHLFDGQALLH
KFDFKEGHVTYHRRFIRTDAYVRAMTEKRIVITEFGTCAFPDPCKNIFSRFFSYFRGVEVTDNALVNI
YPVGEDYYACTETNFITKVNPETLETIKQVDLCNYVSVNGATAHPHIENDGTVYNIGNCFGKNFSIAY
NIVKIPPLQADKEDPISKSEIVVQFPCSDRFKPSYVHSFGLTPNYIVFVETPVKINLFKFLSSWSLWG
ANYMDCFESNETMGVWLHIADKKRKKYINNKYRTSPFNLFHHINTYEDHEFLIVDLCCWKGFEFVYNY
SYLANLRENWEEVKKNARKAPQPEVRRYVLPLNIDKADTGKNLVTLPNTTATAILCSDETIWLEPEVL
FSGPRQAFEFPQINYQKYGGKPYTYAYGLGLNHFVPDRLCKLNVKTKETWVWQEPDSYPSEPIFVSHP
DALEEDDGVVLSVVVSPGAGQKPAYLLILNAKDLSEVARAEVEINIPVTFHGLFKKS

FIG.2I

```
Bovine RPE65 nucleic acid (SEQ ID NO:10)
ATGTCCATCCAAGTTGAACATCCAGCTGGTGGTTACAAGAAACTGTTTGAAACTGTGGAGGAACTATC
CT
CACCGCTCACAGCCCATGTTACAGGCAGGATCCCCCTCTGGCTGACCGGCAGTCTCCTTCGATGTGGG
CC
AGGACTCTTTGAAGTTGGATCGGAACCATTTTACCACCTGTTTGATGGGCAAGCCCTCCTGCACAAGT
TT
GACTTTAAAGAAGGGCATGTCACATACCACAGAAGGTTCATCCGCACTGATGCTTACGTACGGGCAAT
GA
CTGAGAAAAGGATCGTCATAACAGAATTTGGCACCTGTGCTTTCCCAGATCCCTGCAAGAATATATTT
TC
CAGGTTTTTTTCTTACTTCCGAGGAGTGGAGGTTACTGACAATGCCCTTGTTAATATCTACCCAGTGG
GG
GAAGATTACTATGCCTGCACAGAGACCAACTTCATTACAAAGATTAATCCTGAGACCTTGGAAACAAT
TA
AGCAGGTTGACCTTTGCAACTATGTCTCAGTTAATGGAGCCACTGCTCACCCCCACATTGAAAATGAT
GG
GACTGTTTACAACATTGGTAATTGCTTTGGGAAAAATTTTTCAATTGCCTACAATATTGTAAAGATCC
CA
CCACTACAAGCAGACAAGGAAGATCCAATAAGCAAGTCAGAGATCGTTGTACAATTCCCCTGCAGTGA
CC
GATTCAAGCCATCTTACGTCCATAGTTTTGGTTTGACTCCCAACTATATTGTTTTTGTGGAGACACCA
GT
CAAAATTAATCTATTCAAGTTTCTTTCTTCATGGAGTCTTTGGGGAGCCAACTACATGGATTGTTTTG
AG
TCCAATGAAACCATGGGGGTTTGGCTTCATATTGCTGACAAAAAAGAAAAAGTATATCAATAATAA
AT
ACAGGACCTCTCCTTTTAACCTCTTTCATCACATCAATACCTATGAAGACCATGAGTTTCTGATTGTG
GA
TCTCTGTTGCTGGAAAGGATTTGAATTTGTTTATAATTATTTATATTTAGCCAATTTACGTGAGAACT
GG
GAAGAGGTGAAAAAAAATGCCAGAAAGGCTCCTCAGCCTGAAGTTAGGAGATACGTACTTCCTTTGAA
TA
TTGACAAGGCTGACACAGGCAAGAATTTAGTCACACTCCCCAACACAACTGCCACTGCAATTCTGTGC
AG
TGACGAGACCATCTGGCTGGAACCTGAGGTTCTCTTTTCAGGGCCTCGCCAAGCATTTGAGTTTCCTC
AA
ATCAATTACCAGAAGTATGGTGGGAAACCCTACACATATGCATATGGACTTGGTTTGAATCACTTTGT
TC
CAGACAGGCTCTGTAAGCTGAACGTCAAAACTAAAGAAACCTGGGTATGGCAAGAGCCTGATTCATAC
CC
CTCAGAACCTATCTTTGTTTCTCACCCAGATGCCTTGGAGGAAGATGACGGTGTAGTTCTGAGTGTGG
TG
GTGAGCCCTGGGGCAGGACAAAAGCCTGCTTATCTTCTGATTCTGAATGCCAAGGACTTGAGTGAAGT
TG
CCAGGGCTGAAGTGGAGATTAACATCCCTGTCACCTTTCATGGACTGTTCAAAAAATCCTGA
```

FIG.2J

Goat RPE65 protein (SEQ ID NO:11)
MSIQVEHPAGGYKKLFETVEELSSPLTAHVTGRIPLWLTGSLLRCGPGLFEVGSEPFYHLFDGQALLHKF
DFKEGHVTYHRRFIRTDAYVRAMTEKRIVITEFGTCAFPDPCKNIFSRFFSYFRGVEVTDNALVNIYPVG
EDYYACTETNFITKINPETLETIKQVDLCNYVSVNGATAHPHIENDGTVYNIGNCFGKNFSIAYNIVKIP
PLQADKEDPISKSEIVVQFPCSDRFKPSYVHSFGLTPNYIVFVETPVKINLFKFLSSWSLWGANYMDCFE
SNETMGVWLHIADKKRKKYINNKYRTSPFNLFHHINTYEDHEFLIVDLCCWKGFEFVYNYLYLANLRENW
EEVKKNARKAPQPEVRRYVLPLNIDKADTGKNLVTLPNTTATAILCSDETIWLEPEVLFSGPRQAFEFPQ
INYQKYGGKPYTYAYGLGLNHFVPDRLCKLNVKTKETWVWQEPDSYPSEPIFVSHPDALEEDDGVVLSVV
VSPGAGQKPAYLLILNAKDLSEVARAEVEINIPVTFHGLFKKS

FIG.2K

Goat RPE65 nucleic acid (SEQ ID NO:12)
ATGTCCATCCAAGTTGAACATCCAGCTGGTGGTTACAAGAAACTGTTTGAAACTGTGGAGGAACTATCCT
CACCGCTCACAGCCCATGTTACAGGCAGGATCCCCCTCTGGCTGACCGGCAGTCTCCTTCGATGTGGGCC
AGGACTCTTTGAAGTTGGATCGGAACCATTTTACCACCTGTTTGATGGGCAAGCCCTCCTGCACAAGTTT
GACTTTAAAGAAGGGCATGTCACATACCACAGAAGGTTCATCCGCACTGATGCTTACGTACGGGCAATGA
CTGAGAAAAGGATCGTCATAACAGAATTTGGCACCTGTGCTTTCCCAGATCCCTGCAAGAATATATTTC
AGGTTTTTTTCTTACTTCCGAGGAGTGGAGGTTACTGACAATGCCCTTGTTAATATCTACCCAGTGGGG
AAGATTACTATGCCTGCACAGAGACCAACTTCATTACAAAGATTAATCCTGAGACCTTGGAAACAATTA
AGCAGGTTGACCTTTGCAACTATGTCTCAGTTAATGGAGCCACTGCTCACCCCCACATTGAAAATGATGG
GACTGTTTACAACATTGGTAATTGCTTTGGGAAAAATTTTTCAATTGCCTACAATATTGTAAAGATCCCA
CCACTACAAGCAGACAAGGAAGATCCAATAAGCAAGTCAGAGATCGTTGTACAATTCCCCTGCAGTGACC
GATTCAAGCCATCTTACGTCCATAGTTTTGGTTTGACTCCCAACTATATTGTTTTTGTGGAGACACCAGT
CAAAATTAATCTATTCAAGTTTCTTTCTTCATGGAGTCTTTGGGGAGCCAACTACATGGATTGTTTTGAG
TCCAATGAAACCATGGGGGTTTGGCTTCATATTGCTGACAAAAAAGAAAAAGTATATCAATAATAAAT
ACAGGACCTCTCCTTTTAACCTCTTTCATCACATCAATACCTATGAAGACCATGAGTTTCTGATTGTGGA
TCTCTGTTGCTGGAAAGGATTTGAATTTGTTTATAATTATTTATATTTAGCCAATTTACGTGAGAACTGG
GAAGAGGTGAAAAAAAATGCCAGAAAGGCTCCTCAGCCTGAAGTTAGGAGATACGTACTTCCTTTGAATA
TTGACAAGGCTGACACAGGCAAGAATTTAGTCACACTCCCCAACACAACTGCCACTGCAATTCTGTGCAG
TGACGAGACCATCTGGCTGGAACCTGAGGTTCTCTTTTCAGGGCCTCGCCAAGCATTTGAGTTTCCTCAA
ATCAATTACCAGAAGTATGGTGGGAAACCCTACACATATGCATATGGACTTGGTTTGAATCACTTTGTTC
CAGACAGGCTCTGTAAGCTGAACGTCAAAACTAAAGAAACCTGGGTATGGCAAGAGCCTGATTCATACCC
CTCAGAACCTATCTTTGTTTCTCACCCAGATGCCTTGGAGGAAGATGACGGTGTAGTTCTGAGTGTGGTG
GTGAGCCCTGGGCAGGACAAAAGCCTGCTTATCTTCTGATTCTGAATGCCAAGGACTTGAGTGAAGTTG
CCAGGGCTGAAGTGGAGATTAACATCCCTGTCACCTTTCATGGACTGTTCAAAAAATCCTGA

FIG.2L

Dog RPE65 protein (SEQ ID NO:13)
MSIQVEHPAGGYKKLFETVEELSSPLTAHVTGRIPLWLTGSLLRCGPGLFEVGSEPFYHLFDGQALLH
KFDFKEGHVTYHRRFIRTDAYVRAMTEKRIVITEFGTCAFPDPCKNIFSRFFSYFRGVEVTDNALVNV
YPVGEDYYACTETNFITKINPETLETIKQVDLCNYVSVNGATAHPHIENDGTVYNIGNCFGKNFSIAY
NIVKIPPLQADKEDPISKSEVVVQFPCSDRFKPSYVHSFGLTPNYIVFVETPVKINLLKFLSSWSLWG
ANYMDCFESNETMGVWLHIADKKRKKYLNNKYRTSSFNLFHHINTYEDNEFLIVDLCCWKGFEFVYNY
LYLANLRENWEEVKKNARKAPQPEVRRYVLPLNIDKADTGKNLVTLPNTTATATLRSDETIWLEPEVL
FSGPRQAFEFPQINYQKSGGKPYTYAYGLGLNHFVPDRLCKLNVKTKETWVWQEPDSYPSEPIFVSHP
DALEEDDGVVLSVVVSPGAGQKPAYLLILNAKDLSEVARAEVEINIPVTFHGLFKKS

FIG.2M

```
Dog RPE65 nucleic acid (SEQ ID NO:14)
ATGTCCATCCAAGTGGAGCATCCCGCCGGCGGTTACAAGAAGCTGTTTGAAACCGTGGAAGAGCTGTC
GT
CGCCGCTCACCGCCCACGTGACAGGCAGGATCCCGCTCTGGCTCACGGGCAGTCTCCTCCGATGCGGA
CC
GGGGCTCTTCGAGGTTGGATCTGAACCATTTTACCACCTGTTTGACGGACAAGCCCTTCTGCACAAGT
TC
GACTTTAAAGAAGGACACGTCACCTATCACAGAAGGTTCATCCGCACCGATGCTTACGTCCGGGCAAT
GA
CCGAGAAAAGGATCGTCATAACGGAATTTGGCACCTGTGCGTTCCCAGATCCCTGCAAGAATATATTT
TC
CAGGTTTTTTTCTTACTTCCGAGGAGTGGAGGTCACTGACAATGCCCTTGTTAACGTCTACCCAGTAG
GG
GAAGATTACTATGCCTGCACGGAGACCAACTTCATTACAAAGATTAATCCTGAGACCCTGGAGACAAT
TA
AGCAGGTTGATCTCTGCAACTACGTCTCTGTCAATGGAGCCACCGCTCACCCCCACATTGAAAATGAT
GG
GACTGTTTACAACATTGGTAATTGCTTTGGGAAAAATTTTTCGATTGCCTACAATATTGTAAAGATCC
CT
CCACTCCAAGCAGACAAGGAAGATCCAATAAGCAAGTCCGAGGTCGTCGTACAATTCCCCTGCAGCGA
CC
GATTCAAGCCATCGTACGTCCATAGTTTTGGTTTGACTCCCAACTATATTGTTTTTGTGGAGACGCCA
GT
CAAAATTAACCTGCTCAAGTTCCTTTCTTCGTGGAGTCTTTGGGGAGCCAACTACATGGATTGTTTTG
AG
TCCAATGAAACCATGGGGGTTTGGCTTCACATCGCTGACAAAAAAGAAAAAAGTATCTCAATAATAA
GT
ACAGGACCTCTTCCTTTAATCTCTTCCATCATATCAATACTTACGAAGACAATGAGTTTCTGATTGTG
GA
TCTCTGCTGCTGGAAAGGATTTGAATTCGTCTACAATTACTTGTATTTAGCCAATTTACGTGAGAACT
GG
GAAGAGGTGAAAAAAAATGCCAGAAAGGCTCCGCAGCCTGAAGTTAGGAGATACGTGCTTCCTCTGAA
TA
TCGACAAGGCCGACACAGGCAAGAACCTAGTCACCCTCCCCAACACGACGGCCACTGCAACTCTGCGC
AG
CGACGAGACCATCTGGCTGGAACCTGAGGTTCTCTTCTCAGGGCCTCGTCAAGCCTTTGAGTTTCCTC
AA
ATCAACTATCAGAAGTCTGGCGGGAAGCCTTACACGTACGCGTATGGACTTGGCTTGAATCACTTCGT
TC
CGGACAGGCTCTGCAAGCTGAACGTCAAGACTAAAGAAACGTGGGTATGGCAAGAGCCCGACTCATAC
CC
ATCAGAACCCATCTTTGTTTCTCACCCAGATGCCTTGGAAGAAGATGATGGTGTAGTTCTGAGTGTGG
TG
GTGAGCCCTGGGGCAGGACAAAAGCCTGCTTATCTTCTGATTCTGAATGCCAAGGATTTGAGTGAAGT
TG
CCAGGGCTGAAGTGGAGATTAACATCCCTGTCACCTTTCATGGACTGTTCAAAAAATCCTAA
```

FIG.2N

```
Domestic cat RPE65 protein (SEQ ID NO:15)
MSIQVEHPAGGYKKLFETVEELSSPLTAHVTGRIPLWLTGSLLRCGPGLFEVGSEPFYHLFDGQALLHKF
DFKEGHVTYHRRFIRTDAYVRAMTEKRIVITEFGTCAFPDPCKNIFSRFFSYFRGVEVTDNALVNIYPVG
EDYYACTETNFITKINPETLETIKQVDLCNYVSVNGATAHPHIESDGTVYNIGNCFGKNFSIAYNIVKIP
PLQADKEDPISKSEVVVQFPCSDRFKPSYVHSFGLTPNYIVFVETPVKINLFKFLSSWSLWGANYMDCFE
SNETMGVWLHIADKKRRKYLNNKYRTSSFNLFHHINTYEDSEFLIVDLCCWKGFEFVYNYLYLANLRENW
EEVKKNARKAPQPEVRRYVLPLNIDKADTGKNLVTLPNTTATAILCSDETIWLEPEVLFSGPRQAFEFPQ
INYQKYGGKPYTYAYGLGLNHFVPDRLCKLNVKTKETWVWQEPDSYPSEPIFVSHPDALEEDDGVVLSVV
VSPGAGQKPAYLLILNAKDLSEVARAEVEINIPVTFHGLFKKS
```

FIG.2O

```
Cat RPE65 nucleic acid (SEQ ID NO:16)
ATGTCCATCCAAGTTGAACATCCTGCTGGTGGTTACAAGAAACTGTTTGAAACTGTGGAGGAACTGTC
CT
CACCACTCACAGCTCATGTTACAGGCAGGATCCCCCTCTGGCTCACTGGCAGTCTCCTTCGATGTGGG
CC
AGGACTCTTTGAAGTTGGATCTGAACCATTTTACCACCTGTTTGATGGGCAAGCCCTCCTGCACAAGT
TT
GACTTTAAAGAAGGACATGTCACATATCATAGAAGGTTCATCCGCACTGATGCTTACGTTCGGGCAAT
GA
CTGAGAAAAGGATCGTCATAACGGAATTTGGCACTTGTGCTTTCCCAGATCCCTGCAAGAATATATTT
TC
CAGGTTTTTTTCTTACTTTCGAGGAGTGGAGGTCACTGACAATGCCCTTGTTAACATCTACCCAGTAG
GG
GAAGATTACTATGCCTGCACAGAGACCAACTTCATTACAAAGATTAATCCTGAGACCTTGGAGACAAT
TA
AACAGGTTGATCTTTGCAACTATGTCTCTGTCAATGGAGCCACTGCTCACCCCCATATTGAAAGTGAT
GG
AACTGTGTACAACATTGGTAATTGCTTTGGGAAAAATTTTTCAATTGCCTACAATATTGTAAAGATCC
CT
CCACTACAAGCAGACAAGGAAGATCCAATAAGCAAGTCAGAGGTCGTTGTACAATTCCCCTGCAGTGA
CC
GATTCAAGCCATCTTACGTCCATAGTTTTGGTTTGACTCCCAACTATATTGTTTTTGTGGAGACGCCA
GT
CAAAATTAACCTGTTCAAGTTCCTTTCTTCATGGAGTCTTTGGGGAGCCAACTACATGGATTGTTTTG
AG
TCCAATGAAACCATGGGGGTTTGGCTTCATATTGCTGACAAGAAGAGAAGAAAGTATCTCAATAATAA
AT
ACAGGACCTCTTCTTTTAATCTTTTCCATCACATCAATACTTACGAAGACAGTGAGTTTCTGATTGTG
GA
TCTCTGTTGCTGGAAAGGATTTGAATTTGTGTATAATTACCTATATTTAGCCAATTTACGTGAGAACT
GG
GAAGAAGTGAAAAAAAATGCCAGAAAGGCTCCCCAGCCTGAAGTCAGGAGATACGTACTTCCTCTGAA
TA
TTGACAAGGCTGACACAGGCAAGAATTTAGTCACACTCCCCAACACAACTGCCACTGCAATTCTGTGC
AG
TGACGAGACTATCTGGCTGGAACCTGAGGTTCTCTTTTCAGGGCCTCGCCAAGCATTTGAGTTTCCTC
AA
ATCAATTACCAGAAGTATGGTGGGAAACCTTACACATACGCGTATGGACTTGGCCTGAATCACTTTGT
TC
CAGACAGGCTCTGTAAGCTGAATGTTAAAACTAAAGAAACTTGGGTATGGCAAGAGCCTGATTCATAC
CC
ATCAGAACCCATCTTTGTTTCTCACCCAGATGCCTTGGAGGAAGATGATGGTGTAGTTCTGAGTGTGG
TG
GTGAGCCCTGGGGCAGGACAAAAGCCCGCTTATCTTCTGATTCTGAATGCCAAGGACTTGAGTGAAGT
TG
CCAGGGCTGAAGTGGAGATTAACATCCCTGTTACCTTTCATGGGCTGTTCAAAAAATCTTGA
```

FIG.2P

```
Rat RPE65 protein (SEQ ID NO:17)
MSIQIEHPAGGYKKLFETVEELSTPLTAHVTGRIPLWLTGSLLRCGPGLFEVGSEPFYHLFDGQALLH
KFDFKEGHVTYYRRFIRTDAYVRAMTEKRIVITEFGTCAFPDPCKNIFSRFFSYFRGVEVTDNALVNI
YPVGEDYYACTETNFITKINPETLETIKQVDLCNYVSVNGATAHPHIESDGTVYNIGNCFGKNFTVAY
NIIKIPPLKADKEDPINKSEVVVQFPCSDRFKPSYVHSFGLTPNYIVFVETPVKINLFKFLSSWSLWG
ANYMDCFESNESMGVWLHVADKKRRKYFNNKYRTSPFNLFHHINTYEDNGFLIVDLCCWKGFEFVYNY
LYLANLRENWEEVKRNAMKAPQPEVRRYVLPLTIDKADTGRNLVTLPHTTATAILCSDETIWLEPEVL
FSGPRQAFEFPQINYQKCGGKPYTYAYGLGLNHFVPDKLCKLNVKTKEIWMWQEPDSYPSEPIFVSQP
DALEEDDGVVLSVVVSPGAGQKPAYLLVLNAKDLSEIARAEVETNIPVTFHGLFKKP
```

FIG.2Q

```
Rat RPE65 nucleic acid (SEQ ID NO:18)
ATGTCTATCCAAATTGAACACCCTGCTGGTGGCTACAAGAAACTATTTGAAACTGTGGAGGAACTGTC
CA
CACCACTAACAGCTCATGTCACAGGCAGGATTCCCCTCTGGCTCACTGGCAGTCTCCTTCGATGTGGG
CC
AGGGCTCTTTGAAGTTGGATCTGAGCCTTTTTATCACCTGTTTGATGGACAAGCCCTTTTGCACAAGT
TT
GACTTTAAGGAGGGCCATGTCACATACTACAGGAGATTCATCCGCACTGATGCTTATGTTCGAGCAAT
GA
CCGAGAAGAGGATTGTCATAACAGAATTTGGCACCTGTGCTTTTCCAGACCCCTGCAAGAATATATTT
TC
CAGGTTTTTTTCTTACTTTCGAGGAGTAGAGATTACTGACAATGCCCTTGTAAATATTTACCCAGTGG
GA
GAAGATTACTATGCATGCACAGAGACCAACTTTATCACAAAGATTAACCCAGAGACCTTGGAGACTAT
TA
AGCAGGTTGATCTTTGCAACTATGTTTCCGTCAATGGTGCCACTGCTCATCCACATATTGAAAGTGAT
GG
AACAGTTTATAACATTGGCAATTGCTTTGGGAAAAATTTTACAGTTGCCTACAACATTATTAAGATCC
CT
CCACTGAAAGCAGACAAGGAAGACCCAATAAACAAGTCAGAAGTTGTTGTGCAGTTCCCATGCAGTGA
TC
GGTTCAAGCCATCTTATGTACACAGTTTTGGTCTGACTCCCAACTATATCGTTTTGTGGAGACTCCA
GT
CAAAATTAACCTTTTCAAGTTTCTTTCTTCGTGGAGTCTTTGGGGAGCCAACTACATGGACTGTTTCG
AG
TCCAATGAAAGCATGGGGGTTTGGCTTCATGTTGCTGACAAAAAAGAAGAAAATATTTCAATAACAA
AT
ACAGGACCTCCCCTTTCAATCTCTTCCATCATATCAATACTTATGAAGATAATGGGTTTCTGATTGTG
GA
TCTCTGTTGCTGGAAAGGGTTTGAATTTGTTTATAATTACTTATATTTAGCTAATTTACGTGAGAATT
GG
GAAGAAGTAAAACGAAATGCTATGAAAGCTCCTCAGCCTGAAGTCAGGAGATACGTTCTTCCTTTGAC
AA
TTGACAAGGCTGACACAGGCAGAAATTTAGTCACACTTCCCCATACAACTGCCACAGCCATTCTGTGC
AG
TGATGAGACCATATGGCTGGAACCTGAAGTCCTCTTTTCAGGGCCCCGTCAAGCCTTTGAATTTCCTC
AA
ATCAATTACCAGAAATGTGGGGGAAACCTTACACTTATGCATACGGACTTGGATTGAATCACTTTGT
TC
CAGACAAGTTGTGTAAGCTGAATGTCAAAACTAAAGAAATCTGGATGTGGCAAGAACCGGATTCTTAC
CC
ATCTGAACCCATCTTTGTTTCTCAACCGGATGCTCTGGAAGAAGATGATGGTGTAGTTCTGAGTGTGG
TG
GTGAGTCCTGGGGCAGGACAAAAGCCTGCATATCTCCTGGTTCTGAATGCCAAAGACTTGAGTGAAAT
TG
CCAGGGCTGAAGTGGAGACTAATATTCCTGTGACCTTCCATGGACTGTTCAAAAAACCATGA
```

FIG.2R

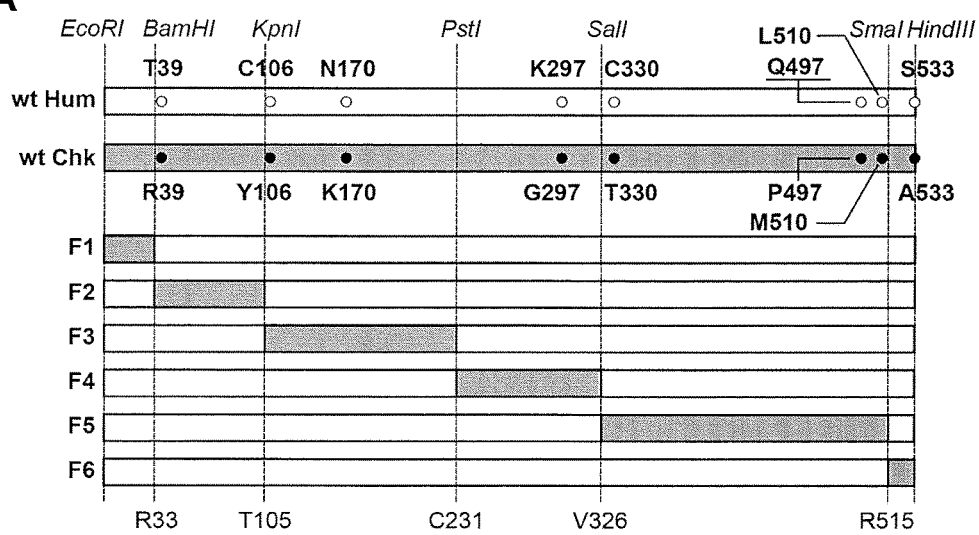
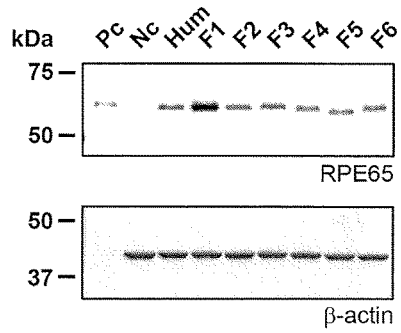
FIGS. 5A-5C

Figure 8 Y. Takahashi et al.

| position | hRPE65 | Substitutions | | | |
|---|---|---|---|---|---|
| 2 | Ser-S | Tyr-Y | Phe-F | His-H | |
| 3 | Ile-I | Ser-S | Thr-T | Cys-C | |
| 26 | Leu-L | Val-V | Ala-A | Ile-I | |
| 39 | Thr-T | Arg-R | Lys-K | His-H | |
| 106 | Cys-C | Tyr-Y | Phe-F | Met-M | His-H |
| 170 | Asn-N | Lys-K | Arg-R | His-H | |
| 297 | Lys-K | Gly-G | Ala-A | | |
| 330 | Cys-C | Thr-T | Ser-S | Met-M | |
| 497 | Gln-Q | Pro-P | His-H | | |
| 510 | Leu-L | Met-M | Cys-C | | |
| 533 | Ser-S | Ala-A | Val-V | Ile-I | Leu-L |
| 220 | Ile-I | Met-M | Cys-C | | |
| 302 | Asn-N | Ile-I | Leu-L | Val-V | |
| 108 | Phe-F | Tyr-Y | His-H | | |
| 158 | Glu-E | Asp-D | | | |
| 169 | Cys-C | Ser-S | Thr-T | | |
| 208 | Lys-K | Arg-R | | | |
| 298 | Lys-K | Arg-R | | | |
| 351 | Glu-E | Asp-D | | | |
| 408 | Leu-L | Ile-I | Val-V | Ala-A | |
| 414 | Gln-Q | His-H | Phe-F | Tyr-Y | |
| 434 | Ala-A | Thr-T | Ser-S | Cys-C | |
| 489 | Val-V | Ile-I | Leu-L | Ala-A | |
| 491 | Val-V | Ile-I | Leu-L | Ala-A | |

FIG.9

SEQUENCE LISTING

```
<160> NUMBER OF SEQ ID NOS: 42

<210> SEQ ID NO 1
<211> LENGTH: 533
<212> TYPE: PRT
<213> ORGANISM: Homo sapiens

<400> SEQUENCE: 1

Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
        115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Thr Met Gly Val Trp
        275                 280                 285

Leu His Ile Ala Asp Lys Lys Arg Lys Lys Tyr Leu Asn Asn Lys Tyr
    290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335
```

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
        355                 360                 365

Val Leu Pro Leu Asn Ile Asp Lys Ala Asp Thr Gly Lys Asn Leu Val
    370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Cys Gly Lys Pro Tyr Thr
            420                 425                 430

Tyr Ala Tyr Gly Leu Gly Leu Asn His Phe Val Pro Asp Arg Leu Cys
        435                 440                 445

Lys Leu Asn Val Lys Thr Lys Glu Thr Trp Val Trp Gln Glu Pro Asp
    450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
        515                 520                 525

Leu Phe Lys Lys Ser
    530

<210> SEQ ID NO 2
<211> LENGTH: 1602
<212> TYPE: DNA
<213> ORGANISM: Homo sapiens

<400> SEQUENCE: 2

```
atgtctatcc aggttgagca tcctgctggt ggttacaaga aactgtttga aactgtggag      60
gaactgtcct cgccgctcac agctcatgta acaggcagga tccccctctg gctcaccggc     120
agtctccttc gatgtgggcc aggactcttt gaagttggat ctgagccatt ttaccacctg     180
tttgatgggc aagccctcct gcacaagttt gactttaaag aaggacatgt cacataccac     240
agaaggttca tccgcactga tgcttacgta cgggcaatga ctgagaaaag gatcgtcata     300
acagaatttg gcacctgtgc tttcccagat ccctgcaaga atatattttc caggtttttt     360
tcttactttc gaggagtaga ggttactgac aatgcccttg ttaatgtcta cccagtgggg     420
gaagattact acgcttgcac agagaccaac tttattacaa agattaatcc agagaccttg     480
gagacaatta gcaggttgat ctttgcaac tatgtctctg tcaatggggc cactgctcac     540
ccccacattg aaaatgatgg aaccgtttac aatattggta attgctttgg aaaaaatttt     600
tcaattgcct acaacattgt aaagatccca ccactgcaag cagacaagga agatccaata     660
agcaagtcag agatcgttgt acaattcccc tgcagtgacc gattcaagcc atcttacgtt     720
catagttttg gtctgactcc caactatatc gtttttgtgg agacaccagt caaaattaac     780
ctgttcaagt tcctttcttc atggagtctt tggggagcca actacatgga ttgttttgag     840
tccaatgaaa ccatgggggt ttggcttcat attgctgaca aaaaaggaa aaagtacctc     900 aataataaat acagaaactc tcctttcaac ctcttccatc acatcaacac ctatgaagac     960
```

-continued

```
aatgggtttc tgattgtgga tctctgctgc tggaaaggat ttgagtttgt ttataattac    1020
ttatatttag ccaatttacg tgagaactgg gaagaggtga aaaaaaatgc cagaaaggct    1080
ccccaacctg aagttaggag atatgtactt cctttgaata ttgacaaggc tgacacaggc    1140
aagaatttag tcacgctccc caatacaact gccactgcaa ttctgtgcag tgacgagact    1200
atctggctgg agcctgaagt tctcttttca gggcctcgtc aagcatttga gtttcctcaa    1260
atcaattacc agaagtattg tgggaaacct tacacatatg cgtatggact tggcttgaat    1320
cactttgttc agataggct ctgtaagctg aatgtcaaaa ctaaagaaac ttgggtttgg     1380
caagagcctg attcataccc atcagaaccc atctttgttt ctcacccaga tgccttggaa    1440
gaagatgatg gtgtagttct gagtgtggtg gtgagcccag gagcaggaca aaagcctgct    1500
tatctcctga ttctgaatgc caaggactta agtgaagttg cccgggctga agtggagatt    1560
aacatccctg tcacctttca tggactgttc aaaaaatctt ga                      1602
```

<210> SEQ ID NO 3
<211> LENGTH: 533
<212> TYPE: PRT
<213> ORGANISM: Chicken

<400> SEQUENCE: 3

```
Met Tyr Ser Gln Val Glu His Pro Ala Gly Gly Tyr Lys Lys Leu Phe
1               5                   10                  15

Glu Thr Val Glu Glu Leu Ser Ser Pro Val Thr Ala His Val Thr Gly
            20                  25                  30

Arg Ile Pro Thr Trp Leu Arg Gly Ser Leu Leu Arg Cys Gly Pro Gly
        35                  40                  45

Leu Phe Glu Val Gly Ala Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Val Arg Thr Asp Ala Tyr Val Arg Ala Met Thr Glu Lys
                85                  90                  95

Arg Ile Val Ile Thr Glu Phe Gly Thr Tyr Ala Tyr Pro Asp Pro Cys
            100                 105                 110

Lys Asn Ile Phe Ser Arg Phe Phe Ser Tyr Phe Lys Gly Val Glu Val
        115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Asp Thr Leu
145                 150                 155                 160

Glu Thr Ile Lys Gln Val Asp Leu Cys Lys Tyr Val Ser Val Asn Gly
                165                 170                 175

Ala Thr Ala His Pro His Val Glu Asn Asp Gly Thr Val Tyr Asn Ile
            180                 185                 190

Gly Asn Cys Phe Gly Lys Asn Phe Ser Leu Ala Tyr Asn Ile Ile Arg
        195                 200                 205

Ile Pro Pro Leu Gln Ala Asp Lys Glu Asp Pro Met Asn Lys Ser Glu
    210                 215                 220

Val Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255
```

```
Val Lys Ile Asn Leu Leu Lys Phe Leu Ser Ser Trp Ser Leu Trp Gly
            260                 265                 270
Ala Asn Tyr Met Asp Cys Phe Glu Ser Asn Glu Thr Met Gly Val Trp
        275                 280                 285
Leu His Val Ala Glu Lys Lys Gly Arg Leu Leu Asn Ile Lys Tyr
    290                 295                 300
Arg Thr Ser Ala Phe Asn Leu Phe His His Ile Asn Thr Phe Glu Asp
305                 310                 315                 320
Asn Gly Phe Leu Ile Val Asp Leu Cys Thr Trp Lys Gly Phe Glu Phe
                325                 330                 335
Val Tyr Asn Tyr Leu Tyr Leu Ala Asn Leu Arg Ala Asn Trp Asp Glu
            340                 345                 350
Val Lys Lys Gln Ala Glu Lys Ala Pro Gln Pro Glu Ala Arg Arg Tyr
        355                 360                 365
Val Leu Pro Leu Arg Ile Asp Lys Ala Asp Thr Gly Lys Asn Leu Val
    370                 375                 380
Thr Leu Pro Tyr Thr Thr Ala Thr Ala Thr Leu Arg Ser Asp Glu Thr
385                 390                 395                 400
Val Trp Leu Glu Pro Glu Val Ile Phe Ser Gly Pro Arg His Ala Phe
                405                 410                 415
Glu Phe Pro Gln Ile Asn Tyr Lys Lys Tyr Gly Gly Lys Pro Tyr Thr
            420                 425                 430
Tyr Thr Tyr Gly Leu Gly Leu Asn His Phe Val Pro Asp Arg Leu Cys
        435                 440                 445
Lys Leu Asn Val Lys Thr Lys Glu Thr Trp Val Trp Gln Glu Pro Asp
    450                 455                 460
Ser Tyr Pro Ser Glu Pro Ile Phe Val Ser His Pro Asp Ala Leu Glu
465                 470                 475                 480
Glu Asp Asp Gly Val Val Leu Ser Ile Val Ile Ser Pro Gly Ser Gly
                485                 490                 495
Pro Lys Pro Ala Tyr Leu Leu Ile Leu Asn Ala Lys Asp Met Ser Glu
            500                 505                 510
Val Ala Arg Ala Glu Val Glu Val Asn Ile Pro Val Thr Phe His Gly
        515                 520                 525
Leu Phe Lys Arg Ala
    530

<210> SEQ ID NO 4
<211> LENGTH: 1602
<212> TYPE: DNA
<213> ORGANISM: Chicken

<400> SEQUENCE: 4
atgtacagcc aggtggagca tcccgcggga ggttacaaga agctcttcga cacagtggag    60
gagctgtcct cacccgtcac tgctcacgtc acaggcagga tccccacctg gctcagaggc   120
agcctcctgc gatgtgggcc tggcctcttt gaagtcgggg cagagccgtt ctaccacctc   180
ttcgatggcc aggcactgct gcacaagttt gacttcaagg agggacatgt cacctaccac   240
cggaggtttg ttaggacaga tgcttatgtg cgagccatga cggagaagag gattgtgata   300
actgaatttg gtacctacgc ctacccagac ccgtgcaaga cattttctc caggttttc    360 tcctacttta aggggtggaa ggtcaccgat aacgccctcg ttaatgtcta ccctgttggt   420
gaggactact acgcctgtac ggagaccaac tttataacca aaattaaccc agacactcta   480
gagacaatta agcaggtgga tctctgcaag tacgtctccg tcaatggggc cacagctcac   540
```

```
cccacgtgg agaacgacgg cacagtttac aacattggca actgctttgg gaaaaatttc      600
tcgctggcct acaacatcat acggattcct ccactccagg cagacaagga ggacccaatg      660
aacaagtcag aggtggtggt gcagttccct tgcagtgaca gatttaagcc ctcctacgtg      720
cacagttttg gcctgacccc aaactacatt gtatttgtcg aaaccccggt gaagatcaac      780
ctcctcaagt tcctctcctc ctggagcctc tggggagcca actacatgga ctgctttgag      840
tccaacgaga ccatggggt ctggcttcac gtggcagaga aaaagaaagg gcggctcctc       900
aatatcaagt accggacctc agccttcaac ctcttccatc acatcaacac cttcgaggat      960
aatgggttcc tcattgtcga cctctgcaca tggaagggat tcgagttcgt ttacaattac     1020
ctctacttag ccaacctccg agcaaactgg gatgaggtaa agaagcaggc tgagaaggcc     1080
ccccagcccg aagcccgcag atacgtgctg cccctccgca tcgacaaggc tgacacaggc     1140
aaaaacttgg tcaccctgcc ctacacgaca gccactgcga cgctgcgcag cgatgagacc     1200
gtctggctgg agccagaagt tatttctca gggccacgcc atgcctttga atttccacag      1260
atcaattaca agaaatacgg tgggaaacca tatacataca cgtatgggct tggactgaat     1320
cactttgttc cagacaggct ttgcaagctg aatgttaaaa caaaggagac ctgggtgtgg     1380
caggagccag attcataccc atcagagcca atcttcgttt cccatccaga tgctctggag     1440
gaggatgatg gggtggtgct gagcattgtg atcagccctg gctcagggcc gaagcctgcc     1500
tacctcctga tcctgaatgc caaggacatg agtgaagtgg ccagggcaga agtggaggtg     1560
aacatccctg tgactttcca tggactcttc aaaagagcat ga                        1602
```

<210> SEQ ID NO 5
<211> LENGTH: 533
<212> TYPE: PRT
<213> ORGANISM: Crab-eating macaque

<400> SEQUENCE: 5

```
Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
        115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190
```

```
Gly Asn Cys Phe Gly Lys Asn Phe Ser Ile Ala Tyr Asn Ile Val Lys
            195                 200                 205

Ile Pro Pro Leu Gln Ala Asp Lys Glu Asp Pro Ile Ser Lys Ser Glu
210                 215                 220

Ile Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Thr Met Gly Val Trp
        275                 280                 285

Leu His Ile Ala Asp Lys Lys Arg Lys Lys Tyr Leu Asn Asn Lys Tyr
    290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
        355                 360                 365

Val Leu Pro Leu Asn Ile Asp Lys Ala Asp Thr Gly Lys Asn Leu Ile
    370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Cys Gly Lys Pro Tyr Thr
            420                 425                 430

Tyr Ala Tyr Gly Leu Gly Leu Asn His Phe Val Pro Asp Arg Leu Cys
        435                 440                 445

Lys Leu Asn Val Lys Thr Lys Glu Thr Trp Val Trp Gln Glu Pro Asp
    450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
        515                 520                 525

Leu Phe Lys Lys Ser
    530

<210> SEQ ID NO 6
<211> LENGTH: 1602
<212> TYPE: DNA
<213> ORGANISM: Crab-eating macaque

<400> SEQUENCE: 6
atgtctatcc aggtcgagca tcctgctggt ggttacaaga aactgtttga aactgtggag    60
gaactgtcct cgccgctcac ggctcatgta acaggcagga tccccctgtg ctcaccggc   120 agtctccttc gatgtgggcc aggactcttt gaagttggat ctgagccatt ttaccacctg   180
```

| | |
|---|---|
| tttgatgggc aagccctcct gcacaagttt gacttcaaag aaggacacgt cacataccac | 240 |
| agaaggttca tccgcactga tgcttacgta cgggcaatga ctgagaaaag gatcgtcata | 300 |
| acagaatttg gcacctgtgc tttcccagat ccctgcaaga atatattttc caggttttt | 360 |
| tcttactttc gaggagtgga ggttaccgac aatgccttg ttaatgtcta cccagtgggg | 420 |
| gaagattact acgcttgcac agagaccaac tttattacaa agattaatcc agagaccttg | 480 |
| gagacaatta gcaggttga tctttgcaac tacgtctccg tcaatggagc cactgctcac | 540 |
| ccccacattg aaaatgatgg aaccgtttac aatattggta attgctttgg aaaaaatttt | 600 |
| tcaattgcct acaacattgt aaagatccca ccactgcaag cagacaagga agatccaata | 660 |
| agcaagtcag agatcgttgt acaattcccc tgcagtgacc gattcaagcc atcttacgtt | 720 |
| catagttttg gtctgactcc caactatatc gttttgtgg agacaccagt caaaattaac | 780 |
| ctgttcaagt tcctttcttc atggagtctt tggggagcca actacatgga ttgctttgag | 840 |
| tccaatgaaa ccatgggggt ttggcttcat attgctgaca aaaaaggaa aaagtacctc | 900 |
| aataataaat acaggacttc tcctttcaac ctcttccatc acatcaacac ctatgaagac | 960 |
| aatgggtttc tgattgtgga tctctgctgc tggaaaggat ttgagtttgt ttataattac | 1020 |
| ttatatttag ccaatttacg tgagaactgg gaagaagtga aaaaaaatgc cagaaaggct | 1080 |
| ccccaacctg aagttaggag atacgtactt cctttgaata ttgacaaggc tgacactggc | 1140 |
| aagaatttaa tcacgctccc caatacaact gccactgcaa ttctgtgcag tgacgagaca | 1200 |
| atctggctgg agcctgaggt tctcttttca gggcctcgcc aagcatttga gtttcctcaa | 1260 |
| atcaattacc agaagtattg tgggaaacct tacacatacg cgtatggact tggcttgaat | 1320 |
| cactttgttc cagataggct ctgtaagctg aatgtcaaaa ctaaagaaac ttgggtttgg | 1380 |
| caagagcctg attcataccc atcagaaccc atctttgttt ctcacccaga tgccttggaa | 1440 |
| gaagatgatg gtgtagttct gagtgtggtg gtgagcccag gagcaggaca aaagcctgct | 1500 |
| tatctcctga ttctgaatgc caaggactta agtgaagttg cccgggctga agtggagatt | 1560 |
| aacatccctg tcacctttca tggactgttc aaaaaatctt ga | 1602 |

<210> SEQ ID NO 7
<211> LENGTH: 533
<212> TYPE: PRT
<213> ORGANISM: Green monkey

<400> SEQUENCE: 7

Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Ser Tyr Phe Arg Gly Val Glu Val
        115                 120                 125

-continued

```
Thr Asp Asn Ala Leu Val Asn Val Tyr Pro Val Gly Glu Asp Tyr Tyr
130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
            165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Thr Met Gly Val Trp
        275                 280                 285

Leu His Ile Ala Asp Lys Lys Arg Lys Lys Tyr Leu Asn Asn Lys Tyr
290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
        355                 360                 365

Val Leu Pro Leu Asn Ile Asp Lys Ala Asp Thr Gly Lys Asn Leu Ile
370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Cys Gly Lys Pro Tyr Thr
            420                 425                 430

Tyr Ala Tyr Gly Leu Gly Leu Asn His Phe Val Pro Asp Arg Leu Cys
        435                 440                 445

Lys Leu Asn Val Lys Thr Lys Glu Thr Trp Val Trp Gln Glu Pro Asp
450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
        515                 520                 525

Leu Phe Lys Lys Ser
        530
```

-continued

<210> SEQ ID NO 8
<211> LENGTH: 1602
<212> TYPE: DNA
<213> ORGANISM: Green monkey

<400> SEQUENCE: 8

| | |
|---|---|
| atgtctatcc aggtcgagca tcctgctggt ggttacaaga aactgtttga aactgtggag | 60 |
| gaactgtcct cgccgctcac agctcatgta acaggcagga tcccctgtg gctcaccggc | 120 |
| agtctccttc gatgtgggcc aggactcttt gaagttggat ctgagccatt ttaccacctg | 180 |
| tttgatgggc aagcccttct gcacaagttt gactttaaag aaggacacgt cacataccac | 240 |
| agaaggttca tccgcactga tgcttacgta cgggccatga ctgagaaaag gatcgtcata | 300 |
| acagaatttg gcacctgtgc tttcccagat ccctgcaaga atatattttc caggtttttt | 360 |
| tcttactttc gaggagtgga ggttaccgac aatgcccttg ttaatgtcta cccagtgggg | 420 |
| gaagactact acgcttgcac agagaccaac tttattacaa agattaatcc agagaccttg | 480 |
| gagacaatta gcaggttga tctttgcaac tacgtctccg tcaatggagc cactgctcac | 540 |
| ccccacattg aaaatgatgg aaccgtttac aatattggta attgctttgg aaaaaatttt | 600 |
| tcaattgcct acaacattgt aaagatccca ccactgcaag cagacaagga agatccaata | 660 |
| agcaagtcag agatcgttgt acaattcccc tgcagtgacc gattcaagcc atcttacgtt | 720 |
| catagttttg gtctgactcc caactatatc gttttgtgg agacaccagt caaaattaac | 780 |
| ctgttcaagt tcctttcttc atggagtctt tggggagcca actacatgga ttgctttgag | 840 |
| tccaatgaaa ccatgggggt ttggcttcat attgctgaca aaaaaggaa aaagtacctc | 900 |
| aataataaat acaggacttc tccttcaac ctcttccatc acatcaacac ctatgaagac | 960 |
| aatgggtttc tgattgtgga tctctgctgc tggaaaggat ttgagtttgt ttataattac | 1020 |
| ttatatttag ccaatttacg tgagaactgg gaagaggtga aaaaaaatgc cagaaaggct | 1080 |
| ccccaacctg aagttaggag atatgtactt cctttgaata ttgacaaggc tgacacaggc | 1140 |
| aagaatttaa tcacgctccc caatacaact gccactgcaa ttctgtgcag tgacgagaca | 1200 |
| atctggctgg agcctgaggt tctcttttca gggcctcgcc aagcgtttga gtttcctcaa | 1260 |
| atcaattacc agaagtattg tgggaaacct tacacatacg catatggact tggcttgaat | 1320 |
| cactttgttc agataggct ctgtaagctg aatgtcaaaa ctaaagaaac ttgggtttgg | 1380 |
| caagagcctg attcataccc atcagaaccc atctttgttt ctcacccaga tgccttggaa | 1440 |
| gaagatgatg gtgtagttct gagtgtggtg gtgagcccag gagcaggaca aaagcctgct | 1500 |
| tatctcctga ttctgaatgc caaggactta agtgaagttg cccgggctga gtggagatt | 1560 |
| aacatccctg tcacctttca cggactgttc aaaaaatctt ga | 1602 |

<210> SEQ ID NO 9
<211> LENGTH: 533
<212> TYPE: PRT
<213> ORGANISM: Bovine

<400> SEQUENCE: 9

Met Ser Ser Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

```
Leu Phe Glu Val Gly Ser Glu Pro Phe Tyr His Leu Phe Asp Gly Gln
 50                  55                  60

Ala Leu Leu His Lys Phe Asp Phe Lys Glu Gly His Val Thr Tyr His
 65                  70                  75                  80

Arg Arg Phe Ile Arg Thr Asp Ala Tyr Val Arg Ala Met Thr Glu Lys
                 85                  90                  95

Arg Ile Val Ile Thr Glu Phe Gly Thr Cys Ala Phe Pro Asp Pro Cys
            100                 105                 110

Lys Asn Ile Phe Ser Arg Phe Ser Tyr Phe Arg Gly Val Glu Val
        115                 120                 125

Thr Asp Asn Ala Leu Val Asn Ile Tyr Pro Val Gly Glu Asp Tyr Tyr
130                 135                 140

Ala Cys Thr Glu Thr Asn Phe Ile Thr Lys Val Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Thr Met Gly Val Trp
        275                 280                 285

Leu His Ile Ala Asp Lys Lys Arg Lys Tyr Ile Asn Asn Lys Tyr
290                 295                 300

Arg Thr Ser Pro Phe Asn Leu Phe His His Ile Asn Thr Tyr Glu Asp
305                 310                 315                 320

His Glu Phe Leu Ile Val Asp Leu Cys Cys Trp Lys Gly Phe Glu Phe
                325                 330                 335

Val Tyr Asn Tyr Ser Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
        355                 360                 365

Val Leu Pro Leu Asn Ile Asp Lys Ala Asp Thr Gly Lys Asn Leu Val
370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Gly Gly Lys Pro Tyr Thr
            420                 425                 430

Tyr Ala Tyr Gly Leu Gly Leu Asn His Phe Val Pro Asp Arg Leu Cys
        435                 440                 445

Lys Leu Asn Val Lys Thr Lys Glu Thr Trp Val Trp Gln Glu Pro Asp
450                 455                 460
```

```
Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
            515                 520                 525

Leu Phe Lys Lys Ser
        530
```

```
<210> SEQ ID NO 10
<211> LENGTH: 1602
<212> TYPE: DNA
<213> ORGANISM: Bovine

<400> SEQUENCE: 10
```

| | | | |
|---|---|---|---|
| atgtccatcc aagttgaaca tccagctggt ggttacaaga aactgtttga aactgtggag | 60 |
| gaactatcct caccgctcac agcccatgtt acaggcagga tccccctctg gctgaccggc | 120 |
| agtctccttc gatgtgggcc aggactcttt gaagttggat cggaaccatt ttaccacctg | 180 |
| tttgatgggc aagccctcct gcacaagttt gactttaaag aagggcatgt cacataccac | 240 |
| agaaggttca tccgcactga tgcttacgta cgggcaatga ctgagaaaag gatcgtcata | 300 |
| acagaatttg gcacctgtgc tttcccagat ccctgcaaga atatattttc caggtttttt | 360 |
| tcttacttcc gaggagtgga ggttactgac aatgcccttg ttaatatcta cccagtgggg | 420 |
| gaagattact atgcctgcac agagaccaac ttcattacaa agattaatcc tgagaccttg | 480 |
| gaaacaatta gcaggttga cctttgcaac tatgtctcag ttaatggagc cactgctcac | 540 |
| ccccacattg aaaatgatgg gactgtttac aacattggta attgctttgg gaaaaatttt | 600 |
| tcaattgcct acaatattgt aaagatccca ccactacaag cagacaagga agatccaata | 660 |
| agcaagtcag agatcgttgt acaattcccc tgcagtgacc gattcaagcc atcttacgtc | 720 |
| catagttttg gtttgactcc caactatatt gttttgtgg agacaccagt caaaattaat | 780 |
| ctattcaagt ttctttcttc atggagtctt tggggagcca actacatgga ttgttttgag | 840 |
| tccaatgaaa ccatgggggt ttggcttcat attgctgaca aaaaaagaaa aaagtatatc | 900 |
| aataataaat acaggacctc tccttttaac ctctttcatc acatcaatac ctatgaagac | 960 |
| catgagtttc tgattgtgga tctctgttgc tggaaaggat ttgaatttgt ttataattat | 1020 |
| ttatatttag ccaatttacg tgagaactgg gaagaggtga aaaaaaatgc cagaaaggct | 1080 |
| cctcagcctg aagttaggag atacgtactt cctttgaata ttgacaaggc tgacacaggc | 1140 |
| aagaatttag tcacactccc caacacaact gccactgcaa ttctgtgcag tgacgagacc | 1200 |
| atctggctgg aacctgaggt tctcttttca gggcctcgcc aagcatttga gtttcctcaa | 1260 |
| atcaattacc agaagtatgg tgggaaaccc tacacatatg catatggact tggtttgaat | 1320 |
| cactttgttc cagacaggct ctgtaagctg aacgtcaaaa ctaaagaaac ctgggtatgg | 1380 |
| caagagcctg attcataccc ctcagaacct atctttgttt ctcacccaga tgccttggag | 1440 |
| gaagatgacg gtgtagttct gagtgtggtg gtgagccctg gggcaggaca aaagcctgct | 1500 |
| tatcttctga ttctgaatgc caaggacttg agtgaagttg ccagggctga agtggagatt | 1560 |
| aacatccctg tcacctttca tggactgttc aaaaaatcct ga | 1602 |

```
<210> SEQ ID NO 11
<211> LENGTH: 533
<212> TYPE: PRT
<213> ORGANISM: Goat

<400> SEQUENCE: 11

Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
        115                 120                 125

Thr Asp Asn Ala Leu Val Asn Ile Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220

Ile Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Thr Met Gly Val Trp
        275                 280                 285

Leu His Ile Ala Asp Lys Lys Arg Lys Lys Tyr Ile Asn Asn Lys Tyr
    290                 295                 300

Arg Thr Ser Pro Phe Asn Leu Phe His His Ile Asn Thr Tyr Glu Asp
305                 310                 315                 320

His Glu Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
        355                 360                 365

Val Leu Pro Leu Asn Ile Asp Lys Ala Asp Thr Gly Lys Asn Leu Val
    370                 375                 380
```

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
            405                 410                 415

Glu Phe Pro Gln Ile Asn Tyr Gln Lys Tyr Gly Gly Lys Pro Tyr Thr
            420                 425                 430

Tyr Ala Tyr Gly Leu Gly Leu Asn His Phe Val Pro Asp Arg Leu Cys
            435                 440                 445

Lys Leu Asn Val Lys Thr Lys Glu Thr Trp Val Trp Gln Glu Pro Asp
            450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
            485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
            515                 520                 525

Leu Phe Lys Lys Ser
    530

<210> SEQ ID NO 12
<211> LENGTH: 1602
<212> TYPE: DNA
<213> ORGANISM: Goat

<400> SEQUENCE: 12
atgtccatcc aagttgaaca tccagctggt ggttacaaga aactgtttga aactgtggag     60
gaactatcct accgctcac agcccatgtt acaggcagga tccccctctg gctgaccggc     120
agtctccttc gatgtgggcc aggactcttt gaagttggat cggaaccatt ttaccacctg    180
tttgatgggc aagccctcct gcacaagttt gactttaaag aagggcatgt cacataccac    240
agaaggttca tccgcactga tgcttacgta cgggcaatga ctgagaaaag gatcgtcata    300
acagaatttg gcacctgtgc tttcccagat ccctgcaaga atatattttc caggtttttt    360
tcttacttcc gaggagtgga ggttactgac aatgcccttg ttaatatcta cccagtgggg    420
gaagattact atgcctgcac agagaccaac ttcattacaa agattaatcc tgagaccttg    480
gaaacaatta agcaggttga ccttttgcaac tatgtctcag ttaatggagc cactgctcac    540
ccccacattg aaaatgatgg gactgtttac aacattggta attgctttgg gaaaaatttt    600
tcaattgcct acaatattgt aaagatccca ccactacaag cagacaagga agatccaata    660
agcaagtcag agatcgttgt acaattcccc tgcagtgacc gattcaagcc atcttacgtc    720
catagttttg gtttgactcc caactatatt gttttttgtgg agacaccagt caaaattaat    780
ctattcaagt ttctttcttc atggagtctt tggggagcca actacatgga ttgttttgag    840
tccaatgaaa ccatgggggt ttggcttcat attgctgaca aaaaagaaa aaagtatatc    900 aataataaat acaggacctc tcctttttaac ctctttcatc acatcaatac ctatgaagac    960
catgagtttc tgattgtgga tctctgttgc tggaaaggat ttgaatttgt ttataattat   1020
ttatatttag ccaatttacg tgagaactgg gaagaggtga aaaaaaatgc cagaaaggct   1080
cctcagcctg aagttaggag atacgtactt cctttgaata ttgacaaggc tgacacaggc   1140
aagaatttag tcacactccc caacacaact gccactgcaa ttctgtgcag tgacgagacc   1200
atctggctgg aacctgaggt tctctttttca gggcctcgcc aagcatttga gtttcctcaa   1260

-continued

```
atcaattacc agaagtatgg tgggaaaccc tacacatatg catatggact tggtttgaat    1320
cactttgttc cagacaggct ctgtaagctg aacgtcaaaa ctaaagaaac ctgggtatgg    1380
caagagcctg attcataccc ctcagaacct atctttgttt ctcacccaga tgccttggag    1440
gaagatgacg gtgtagttct gagtgtggtg gtgagccctg gggcaggaca aaagcctgct    1500
tatcttctga ttctgaatgc caaggacttg agtgaagttg ccagggctga agtggagatt    1560
aacatccctg tcacctttca tggactgttc aaaaaatcct ga                       1602
```

<210> SEQ ID NO 13
<211> LENGTH: 533
<212> TYPE: PRT
<213> ORGANISM: Dog

<400> SEQUENCE: 13

```
Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Ser Tyr Phe Arg Gly Val Glu Val
        115                 120                 125

Thr Asp Asn Ala Leu Val Asn Val Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Asn Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220

Val Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Leu Lys Phe Leu Ser Ser Trp Ser Leu Trp Gly
            260                 265                 270

Ala Asn Tyr Met Asp Cys Phe Glu Ser Asn Glu Thr Met Gly Val Trp
        275                 280                 285

Leu His Ile Ala Asp Lys Lys Arg Lys Lys Tyr Leu Asn Asn Lys Tyr
    290                 295                 300

Arg Thr Ser Ser Phe Asn Leu Phe His His Ile Asn Thr Tyr Glu Asp
305                 310                 315                 320
```

```
Asn Glu Phe Leu Ile Val Asp Leu Cys Cys Trp Lys Gly Phe Glu Phe
            325                 330                 335

Val Tyr Asn Tyr Leu Tyr Leu Ala Asn Leu Arg Glu Asn Trp Glu Glu
        340                 345                 350

Val Lys Lys Asn Ala Arg Lys Ala Pro Gln Pro Glu Val Arg Arg Tyr
    355                 360                 365

Val Leu Pro Leu Asn Ile Asp Lys Ala Asp Thr Gly Lys Asn Leu Val
        370                 375                 380

Thr Leu Pro Asn Thr Thr Ala Thr Ala Thr Leu Arg Ser Asp Glu Thr
385                 390                 395                 400

Ile Trp Leu Glu Pro Glu Val Leu Phe Ser Gly Pro Arg Gln Ala Phe
            405                 410                 415

Glu Phe Pro Gln Ile Asn Tyr Gln Lys Ser Gly Gly Lys Pro Tyr Thr
        420                 425                 430

Tyr Ala Tyr Gly Leu Gly Leu Asn His Phe Val Pro Asp Arg Leu Cys
    435                 440                 445

Lys Leu Asn Val Lys Thr Lys Glu Thr Trp Val Trp Gln Glu Pro Asp
450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
            485                 490                 495

Gln Lys Pro Ala Tyr Leu Leu Ile Leu Asn Ala Lys Asp Leu Ser Glu
        500                 505                 510

Val Ala Arg Ala Glu Val Glu Ile Asn Ile Pro Val Thr Phe His Gly
    515                 520                 525

Leu Phe Lys Lys Ser
    530

<210> SEQ ID NO 14
<211> LENGTH: 1602
<212> TYPE: DNA
<213> ORGANISM: Dog

<400> SEQUENCE: 14
atgtccatcc aagtggagca tcccgccggc ggttacaaga agctgtttga aaccgtggaa      60
gagctgtcgt cgccgctcac cgcccacgtg acaggcagga tcccgctctg gctcacgggc     120
agtctcctcc gatgcggacc ggggctcttc gaggttggat ctgaaccatt ttaccacctg     180
tttgacggac aagcccttct gcacaagttc gactttaaag aaggacacgt cacctatcac     240
agaaggttca tccgcaccga tgcttacgtc cgggcaatga ccgagaaaag gatcgtcata     300
acggaatttg gcacctgtgc gttcccagat ccctgcaaga atatattttc caggtttttt     360
tcttacttcc gaggagtgga ggtcactgac aatgcccttg ttaacgtcta cccagtaggg     420
gaagattact atgcctgcac ggagaccaac ttcattacaa agattaatcc tgagaccctg     480
gagacaatta agcaggttga tctctgcaac tacgtctctg tcaatggagc caccgctcac     540
ccccacattg aaaatgatgg gactgtttac aacattggta attgctttgg gaaaaatttt     600
tcgattgcct acaatattgt aaagatccct ccactccaag cagacaagga agatccaata     660
agcaagtccg aggtcgtcgt acaattcccc tgcagcgacc gattcaagcc atcgtacgtc     720
catagttttg gtttgactcc caactatatt gttttgtgg agacgccagt caaaattaac     780
ctgctcaagt tcctttcttc gtggagtctt tgggagcca actacatgga ttgttttgag     840
tccaatgaaa ccatgggggt ttggcttcac atcgctgaca aaaaaagaaa aaagtatctc     900
```

-continued

```
aataataagt acaggacctc ttcctttaat ctcttccatc atatcaatac ttacgaagac    960
aatgagtttc tgattgtgga tctctgctgc tggaaaggat ttgaattcgt ctacaattac   1020
ttgtatttag ccaatttacg tgagaactgg gaagaggtga aaaaaaatgc cagaaaggct   1080
ccgcagcctg aagttaggag atacgtgctt cctctgaata tcgacaaggc cgacacaggc   1140
aagaacctag tcaccctccc caacacgacg gccactgcaa ctctgcgcag cgacgagacc   1200
atctggctgg aacctgaggt tctcttctca gggcctcgtc aagcctttga gtttcctcaa   1260
atcaactatc agaagtctgg cgggaagcct tacacgtacg cgtatggact tggcttgaat   1320
cacttcgttc cggacaggct ctgcaagctg aacgtcaaga ctaaagaaac gtgggtatgg   1380
caagagcccg actcataccc atcagaaccc atctttgttt ctcacccaga tgccttggaa   1440
gaagatgatg gtgtagttct gagtgtggtg gtgagccctg gggcaggaca aaagcctgct   1500
tatcttctga ttctgaatgc caaggatttg agtgaagttg ccagggctga agtggagatt   1560
aacatccctg tcacctttca tggactgttc aaaaaatcct aa                      1602
```

<210> SEQ ID NO 15
<211> LENGTH: 533
<212> TYPE: PRT
<213> ORGANISM: Domestic cat

<400> SEQUENCE: 15

```
Met Ser Ile Gln Val Glu His Pro Ala Gly Gly Tyr Lys Lys Leu Phe
1               5                   10                  15

Glu Thr Val Glu Glu Leu Ser Ser Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr His
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
        115                 120                 125

Thr Asp Asn Ala Leu Val Asn Ile Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Ser Asp Gly Thr Val Tyr Asn Ile
            180                 185                 190

Gly Asn Cys Phe Gly Lys Asn Phe Ser Ile Ala Tyr Asn Ile Val Lys
        195                 200                 205

Ile Pro Pro Leu Gln Ala Asp Lys Glu Asp Pro Ile Ser Lys Ser Glu
    210                 215                 220

Val Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255
```

Val Lys Ile Asn Leu Phe Lys Phe Leu Ser Ser Trp Ser Leu Trp Gly
                260                 265                 270

Ala Asn Tyr Met Asp Cys Phe Glu Ser Asn Glu Thr Met Gly Val Trp
            275                 280                 285

Leu His Ile Ala Asp Lys Lys Arg Arg Lys Tyr Leu Asn Asn Lys Tyr
        290                 295                 300

Arg Thr Ser Ser Phe Asn Leu Phe His His Ile Asn Thr Tyr Glu Asp
305                 310                 315                 320

Ser Glu Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Lys Asn Ala Arg Lys Ala Pro Gln Pro Glu Val Arg Arg Tyr
        355                 360                 365

Val Leu Pro Leu Asn Ile Asp Lys Ala Asp Thr Gly Lys Asn Leu Val
370                 375                 380

Thr Leu Pro Asn Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Tyr Gly Gly Lys Pro Tyr Thr
            420                 425                 430

Tyr Ala Tyr Gly Leu Gly Leu Asn His Phe Val Pro Asp Arg Leu Cys
        435                 440                 445

Lys Leu Asn Val Lys Thr Lys Glu Thr Trp Val Trp Gln Glu Pro Asp
450                 455                 460

Ser Tyr Pro Ser Glu Pro Ile Phe Val Ser His Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Ile Leu Asn Ala Lys Asp Leu Ser Glu
            500                 505                 510

Val Ala Arg Ala Glu Val Glu Ile Asn Ile Pro Val Thr Phe His Gly
        515                 520                 525

Leu Phe Lys Lys Ser
    530

<210> SEQ ID NO 16
<211> LENGTH: 1602
<212> TYPE: DNA
<213> ORGANISM: Cat

<400> SEQUENCE: 16
atgtccatcc aagttgaaca tcctgctggt ggttacaaga aactgtttga aactgtggag      60
gaactgtcct caccactcac agctcatgtt acaggcagga tccccctctg gctcactggc     120
agtctccttc gatgtgggcc aggactcttt gaagttggat ctgaaccatt ttaccacctg     180
tttgatgggc aagccctcct gcacaagttt gactttaaag aaggacatgt cacatatcat     240
agaaggttca tccgcactga tgcttacgtt cgggcaatga ctgagaaaag gatcgtcata     300
acggaatttg gcacttgtgc tttcccagat ccctgcaaga atatattttc caggtttttt     360
tcttactttc gaggagtgga ggtcactgac aatgcccttg ttaacatcta cccagtaggg     420
gaagattact atgcctgcac agagaccaac ttcattacaa agattaatcc tgagaccttg     480
gagacaatta acaggttgat ctttgcaac tatgtctctg tcaatggagc cactgctcac     540

```
cccatattg aaagtgatgg aactgtgtac aacattggta attgctttgg gaaaaatttt    600
tcaattgcct acaatattgt aaagatccct ccactacaag cagacaagga agatccaata    660
agcaagtcag aggtcgttgt acaattcccc tgcagtgacc gattcaagcc atcttacgtc    720 catagtttg gtttgactcc caactatatt gttttgtgg agacgccagt caaaattaac      780
ctgttcaagt tcctttcttc atggagtctt tggggagcca actacatgga ttgttttgag    840
tccaatgaaa ccatggggt ttggcttcat attgctgaca agaagagaag aaagtatctc     900
aataataaat acaggacctc ttcttttaat cttttccatc acatcaatac ttacgaagac    960
agtgagtttc tgattgtgga tctctgttgc tggaaaggat ttgaatttgt gtataattac    1020
ctatatttag ccaatttacg tgagaactgg gaagaagtga aaaaaaatgc cagaaaggct    1080
ccccagcctg aagtcaggag atacgtactt cctctgaata ttgacaaggc tgacacaggc    1140
aagaatttag tcacactccc caacacaact gccactgcaa ttctgtgcag tgacgagact    1200
atctggctgg aacctgaggt tctcttttca gggcctcgcc aagcatttga gtttcctcaa    1260
atcaattacc agaagtatgg tgggaaacct acacatacg cgtatggact tggcctgaat     1320
cactttgttc cagacaggct ctgtaagctg aatgttaaaa ctaaagaaac ttgggtatgg    1380
caagagcctg attcataccc atcagaaccc atctttgttt ctcacccaga tgccttggag    1440
gaagatgatg gtgtagttct gagtgtggtg gtgagccctg ggcaggaca aaagcccgct     1500 tatcttctga ttctgaatgc caaggacttg agtgaagttg ccaggactga agtggagatt    1560
aacatccctg ttacctttca tgggctgttc aaaaaatctt ga                      1602
```

<210> SEQ ID NO 17
<211> LENGTH: 533
<212> TYPE: PRT
<213> ORGANISM: Rat

<400> SEQUENCE: 17

```
Met Ser Ile Gln Ile Glu His Pro Ala Gly Gly Tyr Lys Lys Leu Phe
1               5                   10                  15

Glu Thr Val Glu Glu Leu Ser Thr Pro Leu Thr Ala His Val Thr Gly
            20                  25                  30

Arg Ile Pro Leu Trp Leu Thr Gly Ser Leu Leu Arg Cys Gly Pro Gly
        35                  40                  45

Leu Phe Glu Val Gly Ser Glu Pro Phe Tyr His Leu Phe Asp Gly Gln
    50                  55                  60

Ala Leu Leu His Lys Phe Asp Phe Lys Glu Gly His Val Thr Tyr Tyr
65                  70                  75                  80

Arg Arg Phe Ile Arg Thr Asp Ala Tyr Val Arg Ala Met Thr Glu Lys
                85                  90                  95

Arg Ile Val Ile Thr Glu Phe Gly Thr Cys Ala Phe Pro Asp Pro Cys
            100                 105                 110

Lys Asn Ile Phe Ser Arg Phe Phe Ser Tyr Phe Arg Gly Val Glu Val
        115                 120                 125

Thr Asp Asn Ala Leu Val Asn Ile Tyr Pro Val Gly Glu Asp Tyr Tyr
    130                 135                 140

Ala Cys Thr Glu Thr Asn Phe Ile Thr Lys Ile Asn Pro Glu Thr Leu
145                 150                 155                 160

Glu Thr Ile Lys Gln Val Asp Leu Cys Asn Tyr Val Ser Val Asn Gly
                165                 170                 175

Ala Thr Ala His Pro His Ile Glu Ser Asp Gly Thr Val Tyr Asn Ile
            180                 185                 190
```

```
Gly Asn Cys Phe Gly Lys Asn Phe Thr Val Ala Tyr Asn Ile Ile Lys
            195                 200                 205

Ile Pro Pro Leu Lys Ala Asp Lys Glu Asp Pro Ile Asn Lys Ser Glu
        210                 215                 220

Val Val Gln Phe Pro Cys Ser Asp Arg Phe Lys Pro Ser Tyr Val
225                 230                 235                 240

His Ser Phe Gly Leu Thr Pro Asn Tyr Ile Val Phe Val Glu Thr Pro
                245                 250                 255

Val Lys Ile Asn Leu Phe Lys Phe Leu Ser Ser Trp Ser Leu Trp Gly
            260                 265                 270

Ala Asn Tyr Met Asp Cys Phe Glu Ser Asn Glu Ser Met Gly Val Trp
        275                 280                 285

Leu His Val Ala Asp Lys Lys Arg Arg Lys Tyr Phe Asn Asn Lys Tyr
    290                 295                 300

Arg Thr Ser Pro Phe Asn Leu Phe His His Ile Asn Thr Tyr Glu Asp
305                 310                 315                 320

Asn Gly Phe Leu Ile Val Asp Leu Cys Cys Trp Lys Gly Phe Glu Phe
                325                 330                 335

Val Tyr Asn Tyr Leu Tyr Leu Ala Asn Leu Arg Glu Asn Trp Glu Glu
            340                 345                 350

Val Lys Arg Asn Ala Met Lys Ala Pro Gln Pro Glu Val Arg Arg Tyr
        355                 360                 365

Val Leu Pro Leu Thr Ile Asp Lys Ala Asp Thr Gly Arg Asn Leu Val
    370                 375                 380

Thr Leu Pro His Thr Thr Ala Thr Ala Ile Leu Cys Ser Asp Glu Thr
385                 390                 395                 400

Ile Trp Leu Glu Pro Glu Val Leu Phe Ser Gly Pro Arg Gln Ala Phe
                405                 410                 415

Glu Phe Pro Gln Ile Asn Tyr Gln Lys Cys Gly Gly Lys Pro Tyr Thr
            420                 425                 430

Tyr Ala Tyr Gly Leu Gly Leu Asn His Phe Val Pro Asp Lys Leu Cys
        435                 440                 445

Lys Leu Asn Val Lys Thr Lys Glu Ile Trp Met Trp Gln Glu Pro Asp
    450                 455                 460

Ser Tyr Pro Ser Glu Pro Ile Phe Val Ser Gln Pro Asp Ala Leu Glu
465                 470                 475                 480

Glu Asp Asp Gly Val Val Leu Ser Val Val Ser Pro Gly Ala Gly
                485                 490                 495

Gln Lys Pro Ala Tyr Leu Leu Val Leu Asn Ala Lys Asp Leu Ser Glu
            500                 505                 510

Ile Ala Arg Ala Glu Val Glu Thr Asn Ile Pro Val Thr Phe His Gly
        515                 520                 525

Leu Phe Lys Lys Pro
530

<210> SEQ ID NO 18
<211> LENGTH: 1602
<212> TYPE: DNA
<213> ORGANISM: Rat

<400> SEQUENCE: 18
atgtctatcc aaattgaaca ccctgctggt ggctacaaga aactatttga aactgtggag      60
gaactgtcca caccactaac agctcatgtc acaggcagga ttcccctctg gctcactggc     120
agtctccttc gatgtgggcc agggctcttt gaagttggat ctgagccttt ttatcacctg     180
```

```
tttgatggac aagccctttt gcacaagttt gactttaagg agggccatgt cacatactac      240
aggagattca tccgcactga tgcttatgtt cgagcaatga ccgagaagag gattgtcata      300
acagaatttg gcacctgtgc ttttccagac ccctgcaaga atatattttc caggttttt       360 tcttactttc gaggagtaga gattactgac aatgcccttg taaatattta cccagtggga      420
gaagattact atgcatgcac agagaccaac tttatcacaa agattaaccc agagaccttg      480
gagactatta gcaggttga  tctttgcaac tatgtttccg tcaatggtgc cactgctcat      540
ccacatattg aaagtgatgg aacagtttat aacattggca attgctttgg gaaaaatttt      600
acagttgcct acaacattat taagatccct ccactgaaag cagacaagga agacccaata      660
aacaagtcag aagttgttgt gcagttccca tgcagtgatc ggttcaagcc atcttatgta      720
cacagttttg gtctgactcc caactatatc gttttgtgg  agactccagt caaaattaac      780
cttttcaagt ttctttcttc gtggagtctt tggggagcca actacatgga ctgtttcgag      840
tccaatgaaa gcatgggggt ttggcttcat gttgctgaca aaaaagaag  aaatatttc       900 aataacaaat acaggacctc ccctttcaat ctcttccatc atatcaatac ttatgaagat      960
aatgggtttc tgattgtgga tctctgttgc tggaaagggt ttgaatttgt ttataattac     1020
ttatatttag ctaatttacg tgagaattgg gaagaagtaa aacgaaatgc tatgaaagct     1080
cctcagcctg aagtcaggag atacgttctt cctttgacaa ttgacaaggc tgacacaggc     1140
agaaatttag tcacacttcc ccatacaact gccacagcca ttctgtgcag tgatgagacc     1200
atatggctgg aacctgaagt cctctttttca gggccccgtc aagcctttga atttcctcaa     1260
atcaattacc agaaatgtgg ggggaaacct tacacttatg catacggact tggattgaat     1320
cactttgttc cagacaagtt gtgtaagctg aatgtcaaaa ctaaagaaat ctggatgtgg     1380
caagaaccgg attcttaccc atctgaaccc atctttgttt ctcaaccgga tgctctggaa     1440
gaagatgatg tgtagttct  gagtgtggtg gtgagtcctg gggcaggaca aaagcctgca     1500
tatctcctgg ttctgaatgc caaagacttg agtgaaattg ccagggctga agtggagact     1560
aatattcctg tgaccttcca tggactgttc aaaaaaccat ga                        1602
```

```
<210> SEQ ID NO 19
<211> LENGTH: 29
<212> TYPE: DNA
<213> ORGANISM: Homo sapiens

<400> SEQUENCE: 19
ccccctctgg ctccgcggca gtctccttc                                         29

<210> SEQ ID NO 20
<211> LENGTH: 29
<212> TYPE: DNA
<213> ORGANISM: Homo sapiens

<400> SEQUENCE: 20
gaaggagact gccgcggagc cagagggggg                                        29

<210> SEQ ID NO 21
<211> LENGTH: 28
<212> TYPE: DNA
<213> ORGANISM: Homo sapiens

<400> SEQUENCE: 21
ggttgatctt tgcaagtatg tctctgtc                                          28
```

```
<210> SEQ ID NO 22
<211> LENGTH: 28
<212> TYPE: DNA
<213> ORGANISM: Homo sapiens

<400> SEQUENCE: 22
gacagagaca tacttgcaaa gatcaacc                                      28

<210> SEQ ID NO 23
<211> LENGTH: 32
<212> TYPE: DNA
<213> ORGANISM: Homo sapiens

<400> SEQUENCE: 23
gattgtggat ctctgcacct ggaaaggatt tg                                 32

<210> SEQ ID NO 24
<211> LENGTH: 32
<212> TYPE: DNA
<213> ORGANISM: Homo sapiens

<400> SEQUENCE: 24
caaatccttt ccaggtgcag agatccacaa tc                                 32

<210> SEQ ID NO 25
<211> LENGTH: 30
<212> TYPE: DNA
<213> ORGANISM: Homo sapiens

<400> SEQUENCE: 25
gcccaggagc aggaccaaag cctgcttatc                                    30

<210> SEQ ID NO 26
<211> LENGTH: 30
<212> TYPE: DNA
<213> ORGANISM: Homo sapiens

<400> SEQUENCE: 26
gataagcagg ctttggtcct gctcctgggc                                    30

<210> SEQ ID NO 27
<211> LENGTH: 32
<212> TYPE: DNA
<213> ORGANISM: Homo sapiens

<400> SEQUENCE: 27
cagaatttgg cacctatgct ttcccagatc cc                                 32

<210> SEQ ID NO 28
<211> LENGTH: 32
<212> TYPE: DNA
<213> ORGANISM: Homo sapiens

<400> SEQUENCE: 28
gggatctggg aaagcatagg tgccaaattc tg                                 32

<210> SEQ ID NO 29
<211> LENGTH: 41
<212> TYPE: DNA
<213> ORGANISM: Homo sapiens

<400> SEQUENCE: 29
gctgacaaaa aaggggaaa gtacctcaat aataaataca g                        41
```

-continued

<210> SEQ ID NO 30
<211> LENGTH: 41
<212> TYPE: DNA
<213> ORGANISM: Homo sapiens

<400> SEQUENCE: 30
ctgtatttat tattgaggta ctttcccctt tttttgtcag c         41

<210> SEQ ID NO 31
<211> LENGTH: 33
<212> TYPE: DNA
<213> ORGANISM: Homo sapiens

<400> SEQUENCE: 31
ctgaatgcca aggacatgag tgaagttgcc cgg                  33

<210> SEQ ID NO 32
<211> LENGTH: 33
<212> TYPE: DNA
<213> ORGANISM: Homo sapiens

<400> SEQUENCE: 32
ccgggcaact tcactcatgt ccttggcatt cag                  33

<210> SEQ ID NO 33
<211> LENGTH: 37
<212> TYPE: DNA
<213> ORGANISM: Homo sapiens

<400> SEQUENCE: 33
ggactgttca aaaaagcttg agcatactcc agcaagc              37

<210> SEQ ID NO 34
<211> LENGTH: 37
<212> TYPE: DNA
<213> ORGANISM: Homo sapiens

<400> SEQUENCE: 34
gcttgctgga gtatgctcaa gcttttttga acagtcc              37

<210> SEQ ID NO 35
<211> LENGTH: 27
<212> TYPE: DNA
<213> ORGANISM: Homo sapiens

<400> SEQUENCE: 35
cagaatttgg tacctgtgct ttcccag                        27

<210> SEQ ID NO 36
<211> LENGTH: 27
<212> TYPE: DNA
<213> ORGANISM: Homo sapiens

<400> SEQUENCE: 36
ctgggaaagc acaggtacca aattctg                        27

<210> SEQ ID NO 37
<211> LENGTH: 30
<212> TYPE: DNA
<213> ORGANISM: Homo sapiens

<400> SEQUENCE: 37
gggtttctga ttgtcgacct ctgctgctgg                     30

```
<210> SEQ ID NO 38
<211> LENGTH: 30
<212> TYPE: DNA
<213> ORGANISM: Homo sapiens

<400> SEQUENCE: 38
ccagcagcag aggtcgacaa tcagaaaccc                                    30

<210> SEQ ID NO 39
<211> LENGTH: 28
<212> TYPE: DNA
<213> ORGANISM: Chicken

<400> SEQUENCE: 39
gcagttcccc tgcagtgaca gatttaag                                      28

<210> SEQ ID NO 40
<211> LENGTH: 28
<212> TYPE: DNA
<213> ORGANISM: Chicken

<400> SEQUENCE: 40
cttaaatctg tcactgcagg ggaactgc                                      28

<210> SEQ ID NO 41
<211> LENGTH: 27
<212> TYPE: DNA
<213> ORGANISM: Chicken

<400> SEQUENCE: 41
gtgaagtggc ccgggcagaa gtggagg                                       27

<210> SEQ ID NO 42
<211> LENGTH: 27
<212> TYPE: DNA
<213> ORGANISM: Chicken

<400> SEQUENCE: 42
cctccacttc tgcccgggcc acttcac                                       27
```

HIGH ISOMEROHYDROLASE ACTIVITY MUTANTS OF HUMAN RPE65

CROSS-REFERENCE TO RELATED APPLICATIONS

The present application is a national stage application of a PCT application having International Application No. PCT/US2015/042263, filed Jul. 27, 2015, which claims priority to U.S. Provisional Application having U.S. Ser. No. 62/031,472, filed Jul. 31, 2014, which claims the benefit under 35 U.S.C. 119(e), the disclosure of which is hereby expressly incorporated herein by reference.

GOVERNMENT SUPPORT

This invention was supported by National Institutes of Health grants EY012231, EY018659, EY019309, and GM104934, a grant from IRRF. The government has certain rights in the invention.

INTRODUCTION

Retinal pigment epithelium (RPE) specific 65-kDa protein (RPE65) is essential for metabolism of vitamin A in the eye and for maintenance of normal vision. It is a key retinoid visual cycle enzyme that catalyzes isomerization of all-trans retinyl ester to 11-cis retinol (11 cROL), the precursor of chromophore of visual pigments. Mutatio ns of RPE65 are associated with inherited retinal dystrophies such as Leber's Congenital Amaurosis (LCA) and Retinitis Pigmentosa (RP). Previous RPE65 gene replacement therapy in RPE65 null-mutants of dog and mouse models displayed promising effects on retinal degeneration. However, mammalian RPE65, such as human RPE65 (hRPE65), has lower specific activity than other retinoid processing enzymes, and high abundance of RPE65 in the RPE (11 µg/eye in bovine) is thus required to generate sufficient 11-cis retinoid for normal vision. This demand for high levels of hRPE65 limits the efficacy of RPE65 gene therapy.

Several vectors for gene delivery, such as adenovirus (AD), recombinant adeno-associated virus (rAAV), lentivirus, plasmid incorporated in nanoparticles and plasmid DNA with electroporation have been used to deliver intact DNA (or reporter genes) to the ocular tissues. Gene delivery into the subretinal space using AD and lentiviral vectors expressing GFP showed widely distributed GFP expression. Recent human clinical trials using rAAV expressing wild type (wt) human RPE65 (rAAV-hRPE65) showed only modest improvements of vision in patients with RP and LCA. However, no prior RPE65 gene therapies have successfully generated full vision recovery in spite of successful gene delivery.

SUMMARY

The presently disclosed inventive concepts include, but are not limited to, mutant mammalian RPE65 proteins or portions thereof that include amino acid sequences having at least 90% identity with at least one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, and SEQ ID NO:17; having isomerohydrolase activity; and having an amino acid substitution in at least one of positions 170 and 297.

In certain non-limiting embodiments, the amino acid substitution in position 170 may be Lys, Arg, or His.

In certain non-limiting embodiments, the amino acid substitution in position 297 may be Gly or Ala.

In certain non-limiting embodiments, the mutant mammalian RPE65 protein or portion thereof may include one or more amino acid substitutions in positions 2, 3, and 26.

In certain non-limiting embodiments, the amino acid substitution in position 2 may be Tyr, Phe, or His.

In certain non-limiting embodiments, the amino acid substitution in position 3 may be Ser, Thr, or Cys In certain non-limiting embodiments, the amino acid substitution in position 26 may be Val, Ala, or Ile.

In certain non-limiting embodiments, the mutant mammalian RPE65 protein or portion thereof may include amino acid substitutions in each of positions 2, 3, 26, 170, and 297, which may be, for example, those described herein.

In certain non-limiting embodiments, the mutant mammalian RPE65 protein or portion thereof has greater isomerohydrolase activity than non-mutated RPE65 protein.

In certain non-limiting embodiments, the mutant mammalian RPE65 protein or portion thereof has greater isomerohydrolase activity than human RPE65 having the amino acid sequence set forth in SEQ ID NO:1 or bovine RPE65 having the amino acid sequence set forth in SEQ ID NO:9.

Also disclosed herein are pharmaceutical compositions that include a mutant mammalian RPE65 protein or portion thereof described herein, disposed in a pharmaceutically-acceptable carrier or vehicle.

Also disclosed herein are nucleic acids that encode a mutant mammalian RPE65 protein or portion thereof described herein.

In certain non-limiting embodiments, the nucleic acid may be disposed within a vector.

In certain non-limiting embodiments, the vector includes a promoter or enhancer sequence operatively-linked to the nucleic acid; and/or includes a stop codon or a poly-A sequence located 3' of the nucleic acid.

In certain non-limiting embodiments, the vector includes an RPE65 promoter sequence that is operatively-linked to the nucleic acid; and/or includes a CMV enhancer/chicken β-actin promoter sequence operatively-linked to the nucleic acid.

In certain non-limiting embodiments, the vector is selected from the group consisting of adenovirus, adeno-associated virus (AAV), nanoparticles, plasmids, and lentivirus.

Also disclosed herein are AAV vectors that include the nucleic acids described herein.

In certain non-limiting embodiments, the vector includes one or more AAV inverted terminal repeat (ITR) sequences.

In certain non-limiting embodiments, the AAV ITR sequences include an ITR sequence of any of: AAV1, AAV2, AAV3, AAV4, AAV5, AAV6, AAV7, AAV8, AAV9, AAV10, AAV11, Rh10, Rh74 or AAV-2i8 AAV serotypes, or a mixture of ITR sequences therefrom.

In certain non-limiting embodiments, the AAV vector includes an AAV capsid sequence.

In certain non-limiting embodiments, the AAV capsid sequence includes a VP1, VP2 and/or VP3 capsid sequence having at least 90% identity to the VP1, VP2 and/or VP3 sequences of AAV1, AAV2, AAV3, AAV4, AAV5, AAV6, AAV7, AAV8, AAV9, AAV10, AAV11, Rh10, Rh74 or AAV-2i8.

Also disclosed are cells that produce AAV vectors of the presently disclosed inventive concepts.

Also disclosed are gene therapy methods of treating conditions related to retinal degeneration in mammalian subjects in need of such treatment, by administering to the subject a therapeutically-effective amount of a vector including a nucleic acid which encodes a mutant mammalian RPE65 protein or portion thereof, wherein the mutant mammalian RPE65 protein or portion thereof is expressed in vivo in retinal cells of the subject and has isomerohydrolase activity. The vector, nucleic acid and mutant mammalian RPE65 protein or portion thereof used in such gene therapy methods may include those described herein.

Also disclosed are methods of treating conditions related to retinal degeneration in subjects in need of such treatment, by administering to the subject a therapeutically-effective amount of at least one mutant mammalian RPE65 protein or a portion thereof described herein, thereby mitigating the condition related to retinal degeneration in the subject.

In certain non-limiting embodiments, the condition related to retinal degeneration is Leber's Congenital Amaurosis or Retinitis pigmentosa.

In certain non-limiting embodiments of the methods described herein, the subject treated is human.

In certain non-limiting embodiments of the methods described herein, the subject is less than 18 years old, less than 15 years old, less than 12 years old, less than 10 years old, between about 8-10 years old, between about 6-10 years old, between about 4-6 years old, between about 1-3 years old or is less than 1 year old or less.

In certain non-limiting embodiments of the methods described herein, the subject may have or be at risk of having retinal degeneration or dystrophy caused by RPE65 mutation.

In certain non-limiting embodiments of the methods described herein, the vector employed may be administered to one or more eyes of the subject.

In certain non-limiting embodiments of the methods described herein, the vector employed may be administered to the subretinal space and/or suprachoroidal space of one or more eyes of the subject.

In certain non-limiting embodiments of the methods described herein, the vector employed is an AAV vector.

In certain non-limiting embodiments of the methods described herein, about $1 \times 10^8$ or more AAV vector genomes are administered to one or more eyes of the subject.

In certain non-limiting embodiments of the methods described herein, about $1 \times 10^8$ to about $1 \times 10^{14}$ AAV vector genomes are administered to one or more eyes of the subject.

In certain non-limiting embodiments of the methods described herein, about $1 \times 10^9$ to about $1 \times 10^{13}$ AAV vector genomes are administered to one or more eyes of the subject.

In certain non-limiting embodiments of the methods described herein, the vector or mutant mammalian RPE65 protein or portion thereof is administered in a volume of about 10 microliters (µl) to about 1,000 µl.

In certain non-limiting embodiments of the methods described herein, the vector or mutant mammalian RPE65 protein or portion thereof is administered in a volume of about 50 µl to about 800 µl.

In certain non-limiting embodiments of the methods described herein, the vector or mutant mammalian RPE65 protein or portion thereof is administered in a volume of about 100 µl to about 600 µl.

In certain non-limiting embodiments of the methods described herein, the vector or mutant mammalian RPE65 protein or portion thereof is administered in a volume of about 200 µl to about 500 µl.

In certain non-limiting embodiments of the methods described herein, a vector or mutant mammalian RPE65 protein or portion thereof described herein is delivered or introduce in cells of the retinal pigment epithelium of one or more eyes of the subject.

Certain embodiments of the presently disclosed inventive concepts include, but are not limited to, mutant mammalian RPE65 proteins or portions thereof that include an amino acid sequence having at least 90% identity with at least one of SEQ ID NO:1, SEQ ID NO:3, SEQ ID NO:5, SEQ ID NO:7, SEQ ID NO:9, SEQ ID NO:11, SEQ ID NO:13, SEQ ID NO:15, and SEQ ID NO:17; and having at least one amino acid substitution that results in an about 2-fold increase to an about 6-fold increase in isomerohydrolase activity as compared to wild-type human RPE65.

In certain non-limiting embodiments, the about 2-fold to about 6-fold increase in isomerohydrolase activity is determined by in vitro isomerohydrolase activity assay.

In certain non-limiting embodiments, the amino acid substitution is Lys, Arg, or His at position 170; and/or Gly or Ala at position 297.

In certain non-limiting embodiments, the amino acid substitution(s) result in an about 3.2-fold increase in isomerohydrolase activity compared to wild-type human RPE65.

In certain non-limiting embodiments, the amino acid substitutions include a Lys, Arg, or His substitution at position 170; a Gly or Ala substitution at position 297; a Tyr, Phe, or His substitution at position 2; a Ser, Thr, or Cys substitution at position 3; and a Val, Ala, or Ile substitution at position 26.

In certain non-limiting embodiments, the amino acid substitutions result in an about 4.4 fold increase in isomerohydrolase activity compared to wild-type human RPE65.

BRIEF DESCRIPTION OF THE DRAWINGS

Several embodiments of the presently disclosed inventive concepts are hereby illustrated in the appended drawings. It is to be noted however, that the appended drawings only illustrate several typical embodiments and are therefore not intended to be considered limiting of the scope of the presently disclosed inventive concepts. Further, in the appended drawings, like or identical reference numerals may be used to identify common or similar elements, and not all such elements may be so numbered. The figures are not necessarily to scale, and certain features and certain views of the figures may be shown exaggerated in scale or in schematic in the interest of clarity and conciseness.

FIG. 1 shows an amino acid sequence alignment of wild type (wt) human RPE65 (hRPE65) and chicken RPE65 (cRPE65). Amino acid residues of cRPE65 identical to those of hRPE65 are indicated as dot ".".

FIGS. 2A-2R show: (A) Amino acid sequence of wild type human RPE65 (SEQ ID NO:1); (B) Nucleic acid sequence encoding human RPE65 (SEQ ID NO:2); (C) Amino acid sequence of chicken RPE65 (SEQ ID NO:3); (D). Nucleic acid sequence encoding chicken RPE65 (SEQ ID NO:4); (E) Amino acid sequence of crab-eating macaque RPE65 (SEQ ID NO:5); (F) Nucleic acid sequence encoding crab-eating macaque RPE65 (SEQ ID NO:6); (G) Amino acid sequence of green monkey RPE65 (SEQ ID NO:7); (H) Nucleic acid sequence encoding green monkey RPE65 (SEQ ID NO:8); (I) Amino acid sequence of bovine RPE65 (SEQ ID NO:9); (J) Nucleic acid sequence encoding bovine RPE65 (SEQ ID NO:10); (K) Amino acid sequence of goat RPE65 (SEQ ID NO:11); (L) Nucleic acid sequence encoding goat RPE65 (SEQ ID NO:12); (M) Amino acid sequence of dog RPE65 (SEQ ID NO:13); (N) Nucleic acid sequence encoding dog RPE65 (SEQ ID NO:14); (O) Amino acid sequence of domestic cat RPE65 (SEQ ID NO:15); (P). Nucleic acid sequence encoding domestic cat RPE65 (SEQ ID NO:16); (Q) Amino acid sequence of rat RPE65 (SEQ ID NO:17); and (R). Nucleic acid sequence encoding rat RPE65 (SEQ ID NO:18).

FIGS. 5A-5C show: Schematic diagram of chimeric human RPE65 mutants and their enzymatic activities. (A) The positions of candidate sites in each fragment and specific restriction sites were represented in the diagram (white bar; hRPE65, gray bar; cRPE65, F1-F6; chimeric hRPE65 replaced with the corresponding cRPE65 fragment). (B) Expression levels of hRPE65, cRPE65 and chimeras were measured by Western blot analysis (Pc; 2.5 µg of bovine RPE microsomal protein, 20 µg of total cellular protein from Hum; hRPE65, Chk; cRPE65, and, F1-F6), and protein levels of RPE65 were semi-quantified by densitometry (C). Enzymatic activities were measured by in vitro isomerohydrolase assay and quantified using generated 11-[$^3$H]-cis retinol and normalized by their relative RPE65 protein levels (C).

FIG. 9 shows non-limiting examples of alternate mutant substitutions in various positions of mammalian RPE65 sequences.

DETAILED DESCRIPTION

Figures 3A, 3B, 3C, 3D:
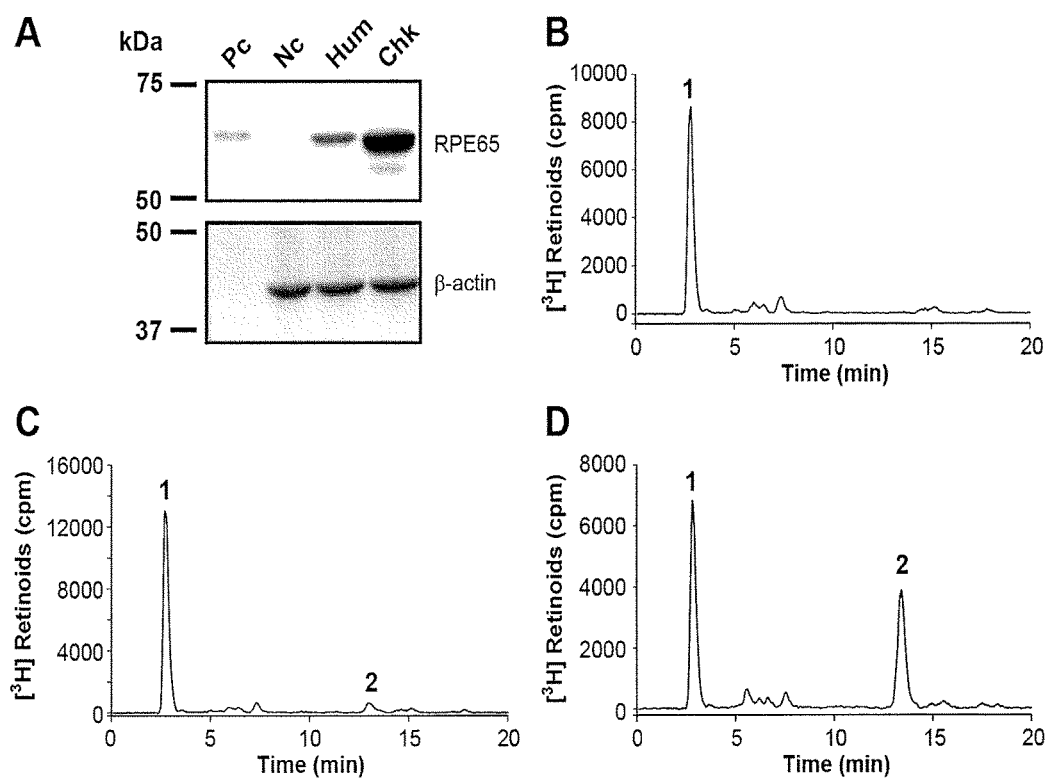
FIGS. 3A-3D show: Expression and enzymatic activities of RPE65 from humans and chicken. Plasmids expressing wt hRPE65, cRPE65 and red fluorescence protein (rfp, negative control) were separately transfected into 293A-LRAT cells. Expression levels and enzymatic activities of hRPE65 and cRPE65 were measured by Western blot analysis (A, Pc; bovine RPE microsomal protein (2.5 µg), Nc; Rfp, Hum; hRPE65 and Chk; cRPE65, 20 µg each) and in vitro isomerohydrolase activity assay, respectively. All-trans-[$^3$H] retinol (0.2 µM) was incubated with 125 µg of total cellular protein from the cells expressing rfp (B), hRPE65 (C) and cRPE65 (D) for 2 hr, and the generated retinoids were analyzed by HPLC. Peak 1, retinyl esters; 2, 11 cROL.

Before describing various embodiments of RPE65 mutants and methods of the presently disclosed inventive concepts in more detail by way of exemplary description, examples, and results, it is to be understood that the presently disclosed inventive concepts are not limited in application to the details of methods and compositions as set forth in the following description. The presently disclosed inventive concepts are capable of other embodiments or of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the presently disclosed inventive concepts may be practiced without these specific details. In other instances, features which are well known to persons of ordinary skill in the art have not been described in detail to avoid unnecessary complication of the description.

Unless otherwise defined herein, scientific and technical terms used in connection with the presently disclosed inventive concepts shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the presently disclosed inventive concepts pertain. All patents, published patent applications, and non-patent publications referenced in any portion of this application are herein expressly incorporated by reference in their entirety to the same extent as if each individual patent or publication was specifically and individually indicated to be incorporated by reference.

All of the compositions and methods of production and application thereof disclosed herein can be made and executed without undue experimentation in light of the present disclosure. While the compositions and methods of the presently disclosed inventive concepts have been described in terms of particular embodiments, it will be apparent to those of skill in the art that variations may be applied to the compositions and/or methods and in the steps or in the sequence of steps of the method described herein without departing from the concept, spirit, and scope of the inventive concepts. All such similar substitutes and modifications apparent to those having ordinary skill in the art are deemed to be within the spirit, scope, and concept of the inventive concepts as defined herein.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal. Non-limiting examples of animals within the scope and meaning of this term include dogs, cats, rats, mice, guinea pigs, horses, goats, cattle, sheep, zoo animals, Old and New World monkeys, nonhuman primates, and humans. In humans, both adults 18 years old and greater, and children less than 18 years old, are appropriate for treatment.

Treatment" refers to therapeutic treatments. The term "treating" refers to administering the composition to a patient for therapeutic purposes.

"Prevention" refers to prophylactic or preventative treatment measures. Administration to a subject can be performed prior to development of an adverse symptom, condition, complication, etc., caused by or associated with the disease. For example, a screen (e.g., genetic) can be used to identify candidate subjects for the compositions and methods of the presently disclosed inventive concepts. Such subjects therefore include those screened positive for an insufficient amount or a deficiency in a functional gene product (protein), or that produce an aberrant, partially functional or non-functional gene product (protein).

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the presently disclosed inventive concept may be designed to provide delayed, controlled, extended, and/or sustained release using formulation techniques which are well known in the art.

The term "effective amount" refers to an amount of an active agent which is sufficient to exhibit a detectable therapeutic effect, without excessive adverse side effects (such as substantial toxicity, irritation and allergic response) commensurate with a reasonable benefit/risk ratio when used in the manner of the inventive concepts. The therapeutic effect may include, for example but not by way of limitation, a partial or complete restoration of vision. For example, to assess a beneficial effect on retinal/visual function testing assays include, electroretinograms (ERGS), pupillometry, and behavioral testing (e.g., an obstacle course with variations in light), before and after treatment.

The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's disease or symptom thereof. A detectable or measurable improvement includes a subjective or objective decrease, reduction, inhibition, suppression, limit or control in the occurrence, frequency, severity, progression, or duration of the disease, or an improvement in a symptom or an underlying cause or a consequence of the disease, or a reversal of the disease.

A successful treatment outcome can lead to a "therapeutic effect," or "benefit" of decreasing, reducing, inhibiting, suppressing, limiting, controlling or preventing the occurrence, frequency, severity, progression, or duration of a disease, or consequences of the disease in a subject. Treatment methods and uses affecting one or more underlying causes of the disease or adverse symptoms are therefore considered to be beneficial. A decrease or reduction in worsening, such as stabilizing the disease, is also a successful treatment outcome.

A therapeutic benefit therefore need not be complete ablation or reversal of the disease, or any one, most or all adverse symptoms, complications, consequences or underlying causes associated with the disease. Thus, a satisfactory endpoint is achieved when there is an incremental improvement such as a partial decrease, reduction, inhibition, suppression, limit, control or prevention in the occurrence, frequency, severity, progression, or duration, or inhibition or reversal of the disease (e.g., stabilizing), over a short or long duration of time (hours, days, weeks, months, etc.). Effectiveness of a method or use, such as a treatment that provides a potential therapeutic benefit or improvement of a disease, can be ascertained by various methods, such as retinal/visual function testing assays including electroretinograms (ERGS), pupillometry, and behavioral testing after treatment, etc.

The term "homologous" or "% identity" as used herein means a nucleic acid (or fragment thereof) or a protein (or a fragment thereof) having a degree of homology to the corresponding natural reference nucleic acid or protein that may be in excess of 70%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff in *Atlas of Protein Sequence and Structure* (1972) Vol. 5, p. 124, National Biochemical Research Foundation, Washington, D.C.). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul (1990) *Proc. Natl. Acad. Sci. USA*, 87, 2264-2268, modified as in Karlin & Altschul (1993) *Proc. Natl. Acad. Sci. USA*, 90, 5873-5877.

In one embodiment "% identity" represents the number of amino acids or nucleotides which are identical at corresponding positions in two sequences of a protein having the same activity or encoding similar proteins. For example, two amino acid sequences each having 100 residues will have 95% identity when 95 of the amino acids at corresponding positions are the same.

Another example of a mathematical algorithm used for comparison of sequences is the algorithm of Myers & Miller (1988) *CABIOS*, 4, 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman (1988) *Proc. Natl. Acad. Sci. USA*, 85, 2444-2448.

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish (1996) Local alignment statistics. In *Methods in Enzymology* (R. Doolittle, ed.) 266, 460-480; Altschul et al. (1990) *Journal of Molecular Biology*, 215, 403-410; Gish & States (1993) *Nature Genetics*, 3: 266-272;

Karlin & Altschul (1993) *Proc. Natl. Acad. Sci. USA*, 90, 5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

The terms "polynucleotide sequence" or "nucleic acid," as used herein, include any polynucleotide sequence which encodes a mutant RPE65 protein product including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The polynucleotide sequence encoding a mutant protein, or encoding a fragment of a mutant protein can be substantially the same as the coding sequence of the endogenous coding sequence as long as it encodes a biologically active mutant protein product. Further, the mutant protein, or fragment of a mutant protein may be expressed using polynucleotide sequence(s) which differ in codon usage due to the degeneracies of the genetic code or allelic variations.

The terms "infection," "transduction," and "transfection" are used interchangeably herein and mean introduction of a gene, nucleic acid, or polynucleotide sequence into cells such that the encoded protein product is expressed. The polynucleotides of the presently disclosed inventive concepts may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of the presently disclosed inventive concepts.

The term "gene therapy" as used herein means genetic modification of cells by the introduction of exogenous DNA or RNA into these cells for the purpose of expressing or replicating one or more peptides, polypeptides, proteins, oligonucleotides, or polynucleotides in vivo for the treatment or prevention of disease or deficiencies in humans or animals. Gene therapy is generally disclosed in U.S. Pat. No. 5,399,346. Any suitable route of administration of the nucleic acid or protein may be employed for providing a subject with pharmaceutical compositions of the presently disclosed inventive concepts. For example, parenteral (subcutaneous, subretinal, suprachoroidal, intramuscular, intravenous, transdermal) and like forms of administration may be employed. Dosage formulations include injections, implants, or other known and effective gene therapy delivery methods.

Genetic delivery vehicles (vectors) for the nucleic acids encoding a protein product of the presently disclosed inventive concepts include any vector suitable for promoting expression of the mutant RPE65 protein product and may optionally comprise an operatively attached promoter sequence which is specific for retinal pigment epithelial cells (e.g., see U.S. Pat. No. 8,785,413). Such gene delivery vehicles are well known in the art to persons having ordinary skill in the art; thus, their detailed description is not deemed necessary herein. For example, a nucleic acid encoding a protein product of the presently disclosed inventive concepts may be contained in adeno-associated virus vectors (e.g., as disclosed in U.S. Pat. Nos. 5,139,941, 5,436,146, and 5,622, 856), an attenuated or gutless adenoviral vectors, (e.g., as disclosed in Morsy, M. A. and Caskey, C. T. (1999) *Mol. Med. Today* 5:18-24; and U.S. Pat. No. 5,935,935), lentiviral vectors (such as are disclosed in U.S. Pat. Nos. 5,665,577; 5,994,136; and 6,013,516), plasmids or synthetic (non-viral) vectors (such as disclosed in U.S. Pat. Nos. 4,394,448 and 5,676,954), and/or nanoparticles (such as disclosed, for example, in U.S. Pat. Nos. 6,217,912; 7,514,098; and 8,323, 618). Alternative viral vectors include, but are not limited to, retroviral vectors (such as are disclosed in U.S. Pat. Nos. 5,672,510; 5,707,865; and 5,817,491), herpes virus vectors (such as are disclosed in U.S. Pat. No. 5,288,641), and sindbis virus vectors and papilloma virus vectors (such as are disclosed in EP 820 773). The vectors may be either monocistronic, bicistronic, or multicistronic.

An adenoviral vector may include essentially the complete adenoviral genome (Shenk, et al. (1984) *Curr. Top. Microbiol. Immunol.*, 111:1-39). Alternatively, the adenoviral vector may be a modified adenoviral vector in which at least a portion of the adenoviral genome has been deleted. Adenoviral vectors may be produced according to He, et al. (1998) *PNAS*, 95:2590-2514; Chartier, et al. (1996) *J. Virol.*, 70:4805-4810; and Hitt, et al. (1995) *Methods in Molecular Genetics*, 7:13-30. Methods of transferring genes into cells using adenoviral vectors have been described in PCT/US95/15947. A number of adenoviral vectors have been developed for the transduction of genes into cells (Berkner, et al. (1988) *BioTechniques* 6:616-629). Constitutive high level expression of the transduced gene products has been achieved. These vectors have the inherent advantage over the retroviral vectors in not requiring replicating cells for infection, making them suitable vectors for somatic gene therapy (Mulligan, R. C. (1993) *Science* 260:926-932). The feasibility for transducing genes associated with glucose metabolism, using adenovirus-mediated transfer in primary rat hepatocytes and myoblast in culture, has been described (Baque, et al. (1994) *Biochem. J.* 304 (Pt 3):1009-1014; Gomez-Foix, et al. (1992) *J. Biol. Chem.* 267:25129-25134).

Vectors which may be used in the methods of the presently disclosed inventive concepts are also described in Narfstrom, et al. (2003) "Functional and structural recovery of the retina after gene therapy in the RPE65 null mutation dog." *Invest. Ophthalmol. Vis. Sci.* 44, 1663-1672; Bennett, et al. (1994) "Adenovirus vector-mediated in vivo gene transfer into adult murine retina." *Invest. Ophthalmol. Vis. Sci.*, 35, 2535-2542; Zhang, et al. (2008) "Distinctive gene transduction efficiencies of commonly used viral vectors in the retina." *Curr. Eye Res.* 33, 81-90; Weber, et al. (2003) "Recombinant adeno-associated virus serotype 4 mediates unique and exclusive long-term transduction of retinal pigmented epithelium in rat, dog, and nonhuman primate after subretinal delivery." *Mol. Ther.,* 7, 774-781; Yokoi, et al. (2007) "Ocular gene transfer with self-complementary AAV vectors." *Invest. Ophthalmol. Vis. Sci.,* 48, 3324-3328; Auricchio, et al. (2001) "Exchange of surface proteins impacts on viral vector cellular specificity and transduction characteristics: the retina as a model." *Hum. Mol. Genet.,* 10, 3075-3081; Pang, et al. (2008) "Comparative analysis of in vivo and in vitro AAV vector transduction in the neonatal mouse retina: effects of serotype and site of administration." *Vision Res.,* 48, 377-385; Yanez-Munoz, et al., (2006) "Effective gene therapy with nonintegrating lentiviral vectors." *Nat. Med.,* 12, 348-353; Bemelmans, et al. (2006) "lentiviral gene transfer of RPE65 rescues survival and function of cones in a mouse model of Leber congenital amaurosis." *PLoS Med.,* 3, 1892-1903; Miyoshi, et al. (1997) "Stable and efficient gene transfer into the retina using an HIV-based lentiviral vector." *Proc. Natl. Acad. Sci. USA,* 94, 10319-10323; Farjo, et al. (2006) Efficient non-viral ocular gene transfer with compacted DNA nanoparticles. *PLoS One,* 1, e38; Kachi, et al. (2005) "Nonviral ocular gene transfer." *Gene Ther.,* 12, 843-851; and Johnson, et al. (2008) "Technical brief: subretinal injection and electroporation into adult mouse eyes." *Mol. Vis.,* 14, 2211-2226.

A recombinant vector (e.g., lenti-, parvo-, AAV) sequence can be packaged-referred to herein as a "particle" for subsequent infection (transduction) of a cell, ex vivo, in vitro or in vivo. Where a recombinant vector sequence is encapsidated or packaged into an AAV particle, the particle can also be referred to as a "rAAV." Such particles include proteins that encapsidate or package the vector genome. Particular examples include viral envelope proteins, and in the case of AAV, capsid proteins.

A vector "genome" refers to the portion of the recombinant plasmid sequence that is ultimately packaged or encapsidated to form a viral (e.g., AAV) particle. In cases where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for recombinant virus production, but is not itself packaged or encapsidated into virus (e.g., AAV) particles.

Thus, a vector "genome" refers to the portion of the vector plasmid that is packaged or encapsidated (e.g., AAV), and which contains a sequence that encodes a mutant RPE65 protein or fragment thereof. The non-vector genome portion of the recombinant plasmid is the "plasmid backbone" that is important for cloning and amplification of the plasmid, e.g., has a selectable marker, such as Kanamycin, but is not itself packaged or encapsidated by virus (e.g., AAV).

AAV vectors can be any serotype. Representative serotypes include AAV1, AAV2, AAV3, AAV4, AAV5, AAV6, AAV7, AAV8, AAV9, AAV10, AAV11, Rh10, Rh74 or AAV-2i8.

Vectors can include additional nucleic acid or protein elements. For example, an AAV vector can include one or two inverted terminal repeat (ITR) sequences of AAV genome retained in the AAV vector. ITR sequences can comprise or be based upon ITRs from any AAV serotype, including, for example, AAV1, AAV2, AAV3, AAV4, AAV5, AAV6, AAV7, AAV8, AAV9, AAV10, AAV11, Rh10, Rh74 or AAV-2i8. Typically, in an AAV vector the nucleic acid encoding mutant RPE65 protein or fragment (portion) thereof is flanked by 5' and/or 3' AAV ITR sequences.

Additional non-limiting examples of nucleic acid sequences include expression control elements (e.g., a promoter, enhancer), introns, poly-Adenine sequence, stop codon, etc. Such sequences including expression control elements can be located at the 5' (i.e., "upstream"), 3' end (i.e., "downstream") of the transcribed sequence or within the sequence (e.g., in an intron). Such sequences including expression control elements can be located adjacent to or at a distance away from the transcribed sequence (e.g., 1-10, 10-25, 25-50, 50-100, 100 to 500, or more nucleotides from the polynucleotide), even at considerable distances.

A specific example of an expression control element is a promoter, which is usually located 5' of the transcribed sequence (a nucleotide sequence that encodes a mutant RPE65 protein or fragment thereof). Another example of an expression control element is an enhancer, which can be located 5' and/or 3' of the transcribed sequence, or within the transcribed sequence.

A "promoter" can refer to a nucleic acid (e.g., DNA) sequence that is located adjacent to a sequence, such as a nucleotide sequence that encodes a mutant RPE65 protein or fragment thereof. A promoter typically increases the amount of nucleic acid expressed to which it is operatively linked as compared to an amount expressed when no promoter exists. An "enhancer" can refer to a sequence that is located adjacent to the sequence, such as a nucleotide sequence that encodes a mutant RPE65 protein or fragment thereof. Enhancer elements are typically located upstream of a promoter element but also function and can be located downstream of a promoter, or be within a DNA sequence. Hence, an enhancer element can be located 10-25, 25-50, 50-100 100-200, 200-300 or more base pairs upstream or downstream of a sequence that encodes a mutant RPE65 protein or fragment thereof. Enhancer elements typically also increase expression of an operatively linked sequence.

As used herein, the term "operable linkage" or "operably linked" refers to a physical or functional juxtaposition of the components so described as to permit them to function in their intended manner. In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Any suitable retinal pigment epithelial-specific promoter sequence may be used with the mutant RPE65 protein-encoding or fragment-encoding nucleic acids. Selection of the promoter to be employed may be made from among a wide number of native, constitutive or inducible promoters that can express the RPE65 protein-encoding or fragment-encoding nucleic acid, for example, in an ocular context.

In one embodiment, a promoter is cell-specific. The term "cell-specific" means that the particular promoter selected for the recombinant vector can direct expression of the selected transgene is a particular ocular cell type. As one example, the promoter is specific for expression in RPE cells. As another example, a promoter is specific for expression in photoreceptor cells.

Representative non-limiting examples of RPE-specific promoters include the RPE-65 promoter, the tissue inhibitor of metalloproteinase 3 (Timp3) promoter, and the tyrosinase promoter. Still other RPE-specific promoters are known in the art (See, e.g., promoters described in International Patent Publication No. WO 00/15822).

Representative non-limiting examples of photoreceptor promoters include the rod opsin promoter, the red-green opsin promoter, the blue opsin promoter, the inter photoreceptor binding protein (IRBP) promoter and the cGMP-.beta.-phosphodiesterase promoter (See, e.g., the promoters described in International Patent Publication No. WO 98/48097.

Expression control elements include ubiquitous or promiscuous promoters/enhancers which are capable of driving expression in many different cell types. In a particular embodiment, a promoter is constitutive. Representative non-limiting examples of constitutive promoters include cytomegalovirus (CMV) immediate early enhancer/chicken β-actin (CβA) promoter-exon 1-intron 1 element, Rous sarcoma virus (RSV) promoter/enhancer sequences, LTR promoter/enhancer, SV40 promoter, CMV promoter, dihydrofolate reductase promoter, and phosphoglycerol kinase (PGK) promoter.

AAV vectors can include capsids of any serotype. Representative AAV capsid serotypes include AAV1, AAV2, AAV3, AAV4, AAV5, AAV6, AAV7, AAV8, AAV9, AAV10, AAV11, Rh10, Rh74 or AAV-2i8. AAV vectors can include capsid chimers or variants of any serotype. Particular AAV capsid variants include capsid variants of such as AAV1, AAV2, AAV3, AAV4, AAV5, AAV6, AAV7, AAV8, AAV9, AAV10, AAV11, Rh10, Rh74 or AAV-2i8, such as a capsid sequence with an amino acid substitution, deletion or insertion/addition.

In certain embodiments of the presently disclosed inventive concepts, compositions comprising a mutant RPE65 protein (and/or a therapeutically effective fragment thereof) are provided in a therapeutic treatment. Alternatively, compositions comprising a nucleotide sequence encoding the mutant RPE65 protein or fragment may be provided in a gene therapy treatment. Also provided are methods of producing these compositions, along with methods of use thereof. In one embodiment, the compositions are utilized for treatment of retinal degeneration-related diseases (dystrophies) or conditions in a subject, including but not limited to Leber's Congenital Amaurosis and Retinitis Pigmentosa (e.g., autosomal recessive retinitis pigmentosa). As noted, a particular treatment method is by gene therapy, for example via adeno-associated virus, lentivirus, plasmid, or nanoparticle. In certain embodiments, the treatment results in a reduction in the occurrence and/or severity of vision loss in a mammalian subject such as a human.

In certain embodiments, the treatments of the presently disclosed inventive concepts use a pharmaceutical composition comprising a vector that expresses the desired mutant RPE65 protein or fragment in vivo under appropriate or suitable conditions or in a suitable host cell. The pharmaceutical compositions can comprise, consist essentially of, or consist of one or more vectors, e.g., expression vectors (viral such as AAV, lenti, etc.), such as in vivo expression vectors, comprising, consisting essentially of, or consisting of and expressing a nucleic acid encoding a mutant RPE65 protein or fragment in combination with a pharmaceutically acceptable carrier, excipient, and/or vehicle. In certain embodiments, the vector comprises, consists essentially of, or consists of and expresses at least one nucleic acid encoding a mutant RPE65 protein or fragment, in a pharmaceutically acceptable carrier, excipient, and/or vehicle. Thus, according to an embodiment of the presently disclosed inventive concepts, the other vector(s) in the composition comprises a nucleic acid encoding a mutant RPE65 protein or fragment.

The pharmaceutically acceptable carrier, vehicle, and/or excipient facilitates transfection and/or improves preservation of the vector. Any pharmaceutically acceptable carriers, vehicles, and excipients known in the art or otherwise contemplated herein may be utilized in accordance with the presently disclosed inventive concepts. For example but not by way of limitation, a pharmaceutically acceptable carrier, vehicle, or excipient can be water, a 0.9% NaCl (e.g., saline) solution, or a phosphate buffer. Other pharmaceutically acceptable carriers, vehicles, and excipients that can be used in the methods of the presently disclosed inventive concepts include, but are not limited to, poly(L-glutamate) or polyvinylpyrrolidone. The pharmaceutically acceptable carrier, vehicle, or excipient may be any compound or combination of compounds facilitating the administration of the vector, increasing the level of expression, and/or increasing the duration of expression.

Doses and dose volumes are discussed herein in the general description and can also be determined by the skilled artisan from this disclosure read in conjunction with the knowledge in the art, without any undue experimentation. For example, the dose volumes can be between about 0.01 and about 2 ml, such as between about 0.02 and about 1 ml. More particular dose volumes can be between about 0.05 and about 0.80 ml, between about 0.10 and about 0.60 ml, or between about 0.20 and about 0.50 ml.

The therapeutic and/or pharmaceutical compositions, in non-limiting embodiments, contain viral particles per dose in a range of, for example, from about $10^4$ to about $10^{11}$ particles, from about $10^5$ to about $10^{10}$ particles, or from about $10^6$ to about $10^9$ particles. In the context of AAV vectors, vector genomes are provided in in a range of, for example, from about $10^4$ to about $10^{14}$ vector genomes, from about $10^5$ to about $10^{13}$ vector genomes, from about $10^6$ to about $10^{13}$ vector genomes, from about $10^7$ to about $10^{13}$ vector genomes, from about $10^8$ to about $10^{13}$ vector genomes, or from about $10^9$ to about $10^{13}$ vector genomes. Such doses/quantities of AAV vector are useful in the methods set forth herein.

The presently disclosed inventive concepts contemplate at least one administration to a subject of an efficient amount of the therapeutic composition made according to the presently disclosed inventive concepts. This administration may be via various routes including, but not limited to, intramuscular, subcutaneous, intraocular, subconjunctival, subretinal, suprachoroidal, or intravascular.

By way of illustration, mutant RPE65 protein or fragments that are encompassed by the proteins/nucleic acids of the presently disclosed inventive concepts include, but are not limited to, mutant RPE65 protein or fragments that are encoded by nucleotide sequences that are not exactly the same as the nucleotide sequences disclosed herein, but wherein the changes in the nucleotide sequences do not change the encoded amino acid sequence, or merely result in conservative substitutions of amino acid residues, deletion and/or addition of one or a few amino acids, substitution of amino acid residues by amino acid analogs that do not significantly affect the properties of the encoded polypeptides, and the like. Examples of conservative amino acid substitutions include, but are not limited to, glycine/alanine substitutions; valine/isoleucine/leucine substitutions; asparagine/glutamine substitutions; aspartic acid/glutamic acid substitutions; serine/threonine/methionine substitutions; lysine/arginine/histidine substitutions; and phenylalanine/tyrosine/tryptophan substitutions.

Accordingly, also included in the presently disclosed inventive concepts are mutant RPE65 proteins and fragments which at least one amino acid residue been removed and a different residue inserted in its place. For a detailed description of protein chemistry and structure, see Schulz, G. E. et al. (1979) *Principles of Protein Structure*, Springer-Verlag, New York, and Creighton, T. E. (1984) *Proteins: Structure and Molecular Principles*, W. H. Freeman & Co., San Francisco. Types of substitutions which may be made are conservative substitutions and are defined herein as exchanges within one of the following groups: (1) Small aliphatic, nonpolar or slightly polar residues: e.g., Ala, Ser, Thr, Gly; (2) Polar, negatively charged residues and their amides: e.g., Asp, Asn, Glu, Gln; and (3) Polar, positively charged residues: e.g., His, Arg, Lys. Pro, because of its unusual geometry, tightly constrains the chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Most substitutions according to the presently disclosed inventive concepts are those which do not produce radical changes in the characteristics of the protein. Even when it is difficult to predict the exact effect of a substitution in advance of doing so, one skilled in the art will appreciate that the effect can be evaluated by routine screening assays, such as an activity assay set forth herein (e.g., the isomerohydrolase activity assay). Modifications of peptide properties including redox or thermal stability, hydrophobicity, susceptibility to proteolytic degradation or the tendency to aggregate with carriers or into multimers are assayed by methods known to the skilled artisan.

Other types of substitutions, variations, additions, deletions and derivatives that result in functional mutant RPE65 protein or fragments and homologs, as described above, are also encompassed by the presently disclosed inventive concepts, and one of skill in the art would readily know how to make, identify, or select such variants or derivatives, and how to test for RPE65 activity of those variants or derivatives. One of ordinary skill in the art may optimize the expression of the mutant RPE65 protein or fragments polypeptides of the presently disclosed inventive concepts to improve expression by any methods known in the art, including but not limited to, by removing cryptic splice sites, by adapting the codon usage by introducing a Kozak consensus sequence before the start codon, by changing the codon usage, or any combination thereof.

In certain embodiments, the presently disclosed inventive concepts comprise a nucleic acid variant having identity or homology of at least 80%, at least 85%, at least 90%, at least 91%, at least 92%, at least 93%, at least 94%, at least 95%, at least 96%, at least 97%, at least 98%, or at least 99% to at least one or more of SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18, and which encodes a mutant RPE65 protein having identity or homology of at least 90%, at least 91%, at least 92%, at least 93%, at least 94%, at least 95%, at least 96%, at least 97%, at least 98%, or at least 99% to a polypeptide encoded by SEQ ID NO:1, SEQ ID NO:3, SEQ ID NO:5, SEQ ID NO:7, SEQ ID NO:9, SEQ ID NO:11, SEQ ID NO:13, SEQ ID NO:15, or SEQ ID NO:17, and which includes at least one or more amino acid substitutions described herein, such as one or more of those described in FIG. 9.

In some embodiments, the DNA encoding the mutant RPE65 protein or fragment is a DNA which hybridizes with a wild type DNA described herein (e.g., SEQ ID NO:2, SEQ ID NO:4, SEQ ID NO:6, SEQ ID NO:8, SEQ ID NO:10, SEQ ID NO:12, SEQ ID NO:14, SEQ ID NO:16, or SEQ ID NO:18) under stringent conditions. By "DNA which hybridizes under stringent conditions" is meant DNA obtained by colony hybridization, plaque hybridization, or Southern blot hybridization using DNA encoding RPE65 protein, specifically including DNA identified after hybridization, using a filter on which colony- or plaque-derived DNA has been immobilized in the presence of 0.7 to 1.0 M NaCl at 65° C. and washing the resulting filter using 0.1× to 2×SSC solutions (the composition of 1×SSC solution comprises 150 mM sodium chloride and 15 mM sodium citrate) at 65° C. Hybridization can be carried out according to a method described, for example, in *Molecular Cloning, A Laboratory Manual, the 2nd edition* (Sambrook, Fritsch, & Maniatis eds., Cold Spring Harbor Laboratory Press, 1989).

Unless otherwise defined, all technical and scientific terms used herein have the same meaning as commonly understood by one of ordinary skill in the art to which this presently disclosed inventive concepts belongs. Although methods and materials similar or equivalent to those described herein can be used in the practice or testing of the presently disclosed inventive concepts, suitable methods and materials are described herein.

Abbreviations used herein include: 11cROL, 11-cis retinol; AD, adenovirus; BTP, 1,3-bis[tris(hydroxymethyl)-methylamino]propane; cRPE65, chicken RPE65; HPLC, High-performance liquid chromatography; hRPE65, human RPE65; LCA, Leber's Congenital Amaurosis; PVDF, Polyvinylidene fluoride; rAAV, recombinant adeno-associated virus; RFP, red-fluorescent protein; RPE, retinal pigment epithelium; RPE65, RPE specific 65-kDa protein; RP, Retinitis Pigmentosa; TBST, Tris-buffered saline with 0.1% Tween-20; wt, wild-type.

All applications, publications, patents and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., nucleic acid, vector, plasmid, a recombinant vector (e.g., rAAV), vector genome, or virus particle) are an example of a genus of equivalent or similar features.

As noted above, as used herein, the singular forms "a", "and," and "the" include plural referents unless the context clearly indicates otherwise. Thus, for example, reference to "a nucleic acid" includes a plurality of such nucleic acids, reference to "a vector" includes a plurality of such vectors, and reference to "a virus" or "particle" includes a plurality of such virions/particles.

As used herein, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 1-20, 10-50, 50-100, 100-1,000, 1,000-3,000, 2,000-4,000, etc.

The presently disclosed inventive concepts will be more readily understood by reference to the following examples and embodiments, which are included merely for purposes of illustration of certain aspects and embodiments of the presently disclosed inventive concepts, and are not intended to be limiting. The following detailed examples and methods describe how to make and use the various mutant proteins of the presently disclosed inventive concepts and are to be construed, as noted above, only as illustrative, and not limitations of the disclosure in any way whatsoever. Those skilled in the art will promptly recognize appropriate variations from the materials and procedures described herein.

Cone-dominant chicken RPE65 (cRPE65-SEQ ID NO:3) is known to possess substantially greater isomerohydrolase activity than that of human RPE65 (hRPE65-SEQ ID NO:1), bovine RPE65 (bRPE65-SEQ ID NO:9) or other mammalian RPE65 protein. As explained in detail below, the enzymatic activities of cRPE65, hRPE65 and mutants of hRPE65 were measured by in vitro isomerohydrolase activity assay, and the retinoid products were analyzed by HPLC. Among the mutants of the presently disclosed inventive concepts analyzed herein, two single point mutants, N170K and K297G, and a double mutant N170K/K297G of hRPE65 exhibited significantly higher catalytic activity than that of wt hRPE65. Further, when an amino terminal fragment (amino acids $1^{Met}$-$33^{Arg}$) of the N170K/K297G double mutant of hRPE65 was replaced with the corresponding n-terminal cRPE65 33-residue fragment, the isomerohydrolase activity was further increased to a level similar to that of cRPE65. This highly efficient isomerohydrolase mutant combination (S2Y/I3S/L26V/N170K/K297G-further described below) can be used, in certain RPE65 gene therapy embodiments of the present disclosure to improve vision in mammalian subjects having or at risk of having retinal degeneration caused by RPE65 mutations, including but not limited to, humans.

In the work presently disclosed, using site-directed mutagenesis, a number of residues of hRPE65 were substituted with their positional counterparts of cRPE65 (alignment shown in FIG. 1) and evaluated the isomerohydrolase activities of the generated hRPE65 mutants. The results are shown and discussed below.

EXPERIMENTAL PROCEDURES

Site-Directed Mutagenesis.

cDNAs encoding Wild-type (wt) hRPE65 protein (SEQ ID NO:1) and cRPE65 protein (SEQ ID NO:3) were subcloned into cloning vectors as described previously (Moiseyev, et al. (2005) "RPE65 Is the Isomerohydrolase in the Retinoid Visual Cycle." *Proc. Natl. Acad. Sci. USA*, 102, 12413-12418; and Moiseyev, et al. (2008) "RPE65 from Cone-dominant Chicken Is a More Efficient Isomerohydrolase Compared with That from Rod-dominant Species." *J. Biol. Chem.*, 283, 8110-8117). Selected residues in hRPE65 were replaced by their counterparts in cRPE65 using the QuickChange site-directed mutagenesis kit (Stratagene, La Jolla, Calif.) following the manufacturer's protocol. The introduced mutations were confirmed by sequencing from both strands using ABI-3730 DNA sequencer (Applied Biosystems, Foster City, Calif.) and subcloned into an expression vector, pcDNA3.1 (-) (Invitrogen, Carlsbad, Calif.). Following the sequence confirmation, the expression constructs were purified by QIAfilter Maxi Prep kit (Qiagen, Valencia, Calif.). Further, the hRPE65 cDNA (SEQ ID NO:2) and cRPE65 cDNA (SEQ ID NO:4) were individually subcloned into pUC18. To generate 6 restriction fragments of hRPE65 and cRPE65, unique restriction enzyme sites were introduced without changing amino acid sequence (see FIG. 5A). Each fragment of hRPE65 was replaced by its counterpart of cRPE65 using the introduced restriction enzyme sites. All primer sets (SEQ ID NOS:19-42) used in this study are shown in Table 1.

TABLE 1

Primer sets.

| Name | Sequence | SEQ ID NO. |
|---|---|---|
| Hum T39R-Fwd | 5'-CCCCCTCTGGCTCCGCGGCAGTCTCCTTC-3' | SEQ ID NO: 19 |
| Hum T39R-Rev | 5'-GAAGGAGACTGCCGCGGAGCCAGAGGGGG-3 | SEQ ID NO: 20 |
| Hum N170K-Fwd | 5'-GGTTGATCTTTGCAAGTATGTCTCTGTC-3' | SEQ ID NO: 21 |
| Hum N170K-Rev | 5'-GACAGAGACATACTTGCAAAGATCAACC-3' | SEQ ID NO: 22 |
| Hum C330T-Fwd | 5'-GATTGTGGATCTCTGCACCTGGAAAGGATTTG-3' | SEQ ID NO: 23 |
| Hum C330T-Rev | 5'-CAAATCCTTTCCAGGTGCAGAGATCCACAATC-3' | SEQ ID NO: 24 |
| Hum Q497P-Fwd | 5'-GCCCAGGAGCAGGACCAAAGCCTGCTTATC-3' | SEQ ID NO: 25 |

TABLE 1-continued

Primer sets.

| Name | Sequence | SEQ ID NO. |
|---|---|---|
| Hum Q497P-Rev | 5'-GATAAGCAGGCTTTGGTCCTGCTCCTGGGC-3' | SEQ ID NO: 26 |
| Hum C106Y-Fwd | 5'-CAGAATTTGGCACCTATGCTTTCCCAGATCCC-3' | SEQ ID NO: 27 |
| Hum C106Y-Rev | 5'-GGGATCTGGGAAAGCATAGGTGCCAAATTCTG-3' | SEQ ID NO: 28 |
| Hum K297G-Fwd | 5'-GCTGACAAAAAAGGGGAAAGTACCTCAATAATAAATACAG-3' | SEQ ID NO: 29 |
| Hum K297G-Rev | 5'-CTGTATTTATTATTGAGGTACTTTCCCCTTTTTTTGTCAGC-3' | SEQ ID NO: 30 |
| Hum L510M-Fwd | 5'-CTGAATGCCAAGGACATGAGTGAAGTTGCCCGG-3' | SEQ ID NO: 31 |
| Hum L510M-Rev | 5'-CCGGGCAACTTCACTCATGTCCTTGGCATTCAG-3' | SEQ ID NO: 32 |
| Hum S533A-Fwd | 5'-GGACTGTTCAAAAAAGCTTGAGCATACTCCAGCAAGC-3 | SEQ ID NO: 33 |
| Hum S533A-Rev | 5'-GCTTGCTGGAGTATGCTCAAGCTTTTTTGAACAGTCC-3' | SEQ ID NO: 34 |
| Hum KpnI-Fwd | 5'-CAGAATTTGGTACCTGTGCTTTCCCAG-3' | SEQ ID NO: 35 |
| Hum KpnI-Rev | 5'-CTGGGAAAGCACAGGTACCAAATTCTG-3' | SEQ ID NO: 36 |
| Hum SalI-Fwd | 5'-GGGTTTCTGATTGTCGACCTCTGCTGCTGG-3' | SEQ ID NO: 37 |
| Hum SalI-Rev | 5'-CCAGCAGCAGAGGTCGACAATCAGAAACCC-3' | SEQ ID NO: 38 |
| ChkPstI-Fwd | 5'-GCAGTTCCCCTGCAGTGACAGATTTAAG-3' | SEQ ID NO: 39 |
| ChkPstI-Rev | 5'-CTTAAATCTGTCACTGCAGGGGAACTGC-3' | SEQ ID NO: 40 |
| Chk SmaI-Fwd | 5'-GTGAAGTGGCCCGGGCAGAAGTGGAGG-3' | SEQ ID NO: 41 |
| Chk SmaI-Rev | 5'-CCTCCACTTCTGCCCGGGCCACTTCAC-3' | SEQ ID NO: 42 |

Plasmid Transfection.

Constructed plasmids expressing wt hRPE65, cRPE65, and the hRPE65 mutants were purified using a QIAfilter Maxi Prep kit (Qiagen, Valencia, Calif.) and transfected into 293A-LRAT cells, a cell line stably expressing human LRAT (45), using Fugene 6 transfection reagent (Roche, Indianapolis, Ind.) or polyethylenimine (PEI, Polysciences, Inc., Warrington, Pa.; 1 mg/ml, pH 7.4, 2:1 of PEI:DNA ratio), and the culture media were replaced at 6 hr following the transfection. At 48 hr post transfection, cells were harvested by cell scraper and rinsed twice with ice-cold PBS. Protein levels and enzymatic activities of wt hRPE65 and its mutants were confirmed by Western blot analyses and in vitro isomerohydrolase activity assay.

Western Blot Analysis.

Total cellular protein concentrations were measured using a Bradford assay. Equal amounts of total cellular proteins (20 rig) of 293A-LRAT cells expressing wt hRPE65 and cRPE65, and hRPE65 mutants and bovine RPE microsomal proteins (2.5 µg) as a positive control were resolved by electrophoresis through 8% Tris-glycine SDS polyacrylamide gel and electrotransferred onto an immobilon PVDF membrane (Millipore, Billerica, Mass.) unless specified. The membrane was blocked with 5% (wt/vol) non-fat dry milk in TBST (Tris-buffered saline with 0.1% Tween-20) for 30 min and subsequently incubated overnight at 4° C. with a 1:1,000 dilution of an anti-RPE65 polyclonal antibody (e.g., see Ma, et al. (2001) "Expression, purification, and MALDI analysis of RPE65." *Invest. Ophthalmol. Vis. Sci.*, 42, 1429-1435) to identify the key residues and 1:50,000 dilution of an anti-β-actin monoclonal antibody (Sigma-Aldrich, St. Louis, Mo.). We used another RPE65 antibody (Moiseyev, et al. (2008) "RPE65 from Cone-dominant Chicken Is a More Efficient Isomerohydrolase Compared with That from Rod-dominant Species." *J. Biol. Chem.*, 283, 8110-8117) to compare the expression levels of cRPE65 and chimeric mutants of RPE65 to avoid the immunoreactivity difference on fragment 3. After four washes with TBST, the membrane was incubated in a light shielding container for 1.5 hr with 1:25,000 dilution of goat anti-mouse IgG conjugated with DyLight-549 and goat anti-rabbit IgG conjugated with DyLight-649 (Pierce, Rockford, Ill.), and the bands were detected using FluorChem Q imaging system (AlphaInnotech, San Leandro, Calif.). The signal intensities were semi-quantified by densitometry using AlphaView Q software (AlphaInnotech, San Leandro, Calif.), and averaged from at least 3 independent experiments.

Isomerohydrolase Activity Assay.

293A-LRAT cells were separately transfected with plasmids expressing wt human and chicken RPE65 and hRPE65 mutants. 293A-LRAT cells expressing red fluorescence protein (rfp) were used as a negative control. Cells were lysed by sonication in a reaction buffer (10 mM 1,3-bis[tris (hydroxymethyl)-methylamino]propane (BTP), pH 8.0, 100 mM NaCl). All-trans [11,12-$^3$H]-retinol (1 mCi/ml, 45.5 Ci/mmol, American Radiolabeled Chemical, Inc., St. Louis, Mo.) in N,N-dimethyl formamide was used as the substrate for the isomerohydrolase assay. For each reaction, total cellular proteins (125 µg) were added into 200 µl of reaction buffer (10 mM BTP, pH 8.0, 100 mM NaCl) containing 0.2 µM of all-trans retinol, 1% BSA and 25 µM of cellular retinal aldehyde-binding protein. The reaction was stopped, and retinoids were extracted with 300 µl of cold methanol and 300 µl of hexane. The generated retinoids were analyzed by normal phase HPLC. The peak of each retinoid isomer was identified based on its characteristic retention time and absorption spectrum of retinoid standards. Isomerohydrolase activity was calculated from the area of the 11 cROL peak using Radiomatic 610TR software (Perkin Elmer, Boston, Mass.) with synthetic 11-cis [$^3$H]-retinol as the standard. To minimize the variation of the transfection efficiency, all in vitro activity assays of the mutants were conducted side-by-side with wt hRPE65, and the catalytic activities were expressed as values relative to that of wt hRPE65 unless specified.

Results

Comparison of expression and enzymatic activities of hRPE65 and cRPE65.

Plasmids expressing red fluorescence protein (rfp; negative control), hRPE65 and cRPE65 were separately transfected into the 293A-LRAT cells and cultured for 48 hr. The expression levels and enzymatic activities of hRPE65 and cRPE65 were verified by Western blot analysis (FIG. 3A) and in vitro isomerohydrolase assay. Both hRPE65 and cRPE65, but not negative control protein rfp, converted all-trans retinyl ester into 11 cROL, the product of isomerohydrolase (FIGS. 3B-3D). cRPE65 produced substantially higher levels of 11 cROL than that of wt hRPE65 after the normalization to its RPE65 protein level, indicating a higher enzymatic activity of cRPE65.

Selection of Mutants.

Eight residues from various positions in cRPE65 were selected for examining the difference in the isomerohydrolase activity between hRPE65 and cRPE65 (see FIG. 1). In order to evaluate the contribution of these residues to isomerohydrolase activity, a series of point mutations of the 8 candidate residues in hRPE65 were generated by site-directed mutagenesis. For in vitro enzyme activity assays, the effect of substitution of Thr at position 39, Asn at position 170, Cys at position 330 and Gln at position 497 in hRPE65 was examined in a first experimental set. Substitutions of Cys at position 106, Lys at position 297, Leu at position 510, and Ser at position 533 were examined in a second experimental set.

Impacts of Site-Directed Point Mutations on Protein Levels and Catalytic Activities of hRPE65.

Figures 4A, 4B, 4C, 4D, 4E, 4F, 4G:
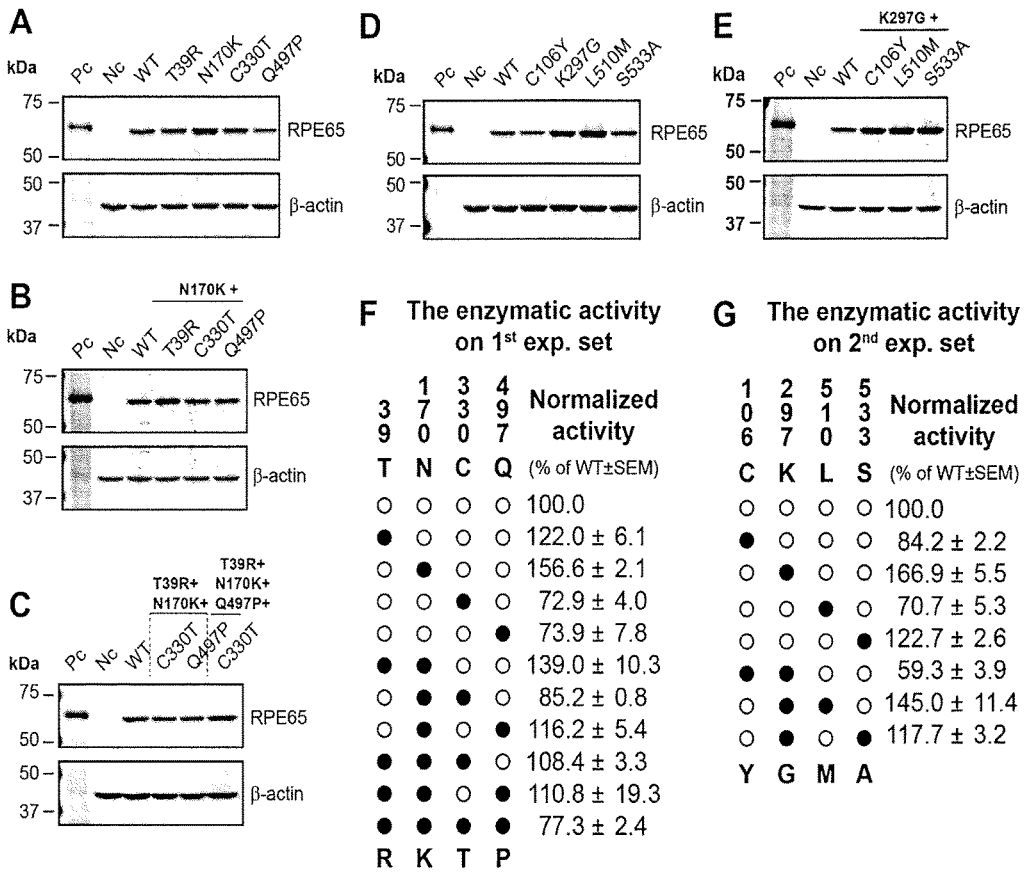
FIGS. 4A-4G show: Impacts of site-directed mutations on isomerohydrolase activity and protein level of RPE65. Plasmids expressing wt hRPE65 and cRPE65, and the indicated hRPE65 mutants were separately transfected into 293A-LRAT cells and cultured for 48 hr. (A-D) The equal amount of total proteins from cell lysates (20 µg) was used for Western blotting using an antibody specific for RPE65, with an anti-β-actin antibody as loading control (A; single, B; double, C; triple and quadruple mutants in the 1$^{st}$ experimental set, and D; single, E; double mutants in the 2$^{nd}$ experimental set. Pc; positive control (bovine RPE microsomal protein, 2.5 µg) Nc; negative control (red fluorescence protein), WT; wt hRPE65). RPE65 levels were semi-quantified by densitometry and normalized by β-actin levels. (F and G) In vitro activity assays were performed with the same batch of samples of Western blot analyses. Isomerohydrolase activities were quantified by generated 11-[$^3$H]-cis retinol from 3 independent measurements and normalized by their relative RPE65 protein levels. Values were expressed as relative activity (% of wt hRPE65 activity, mean±SEM, n=3). In the enzymatic activity tables (F and G), human (○) and chicken (●) residues were indicated as white and black circles, respectively. The vertical numbers indicate the positions of candidate residues. Letters above and below the panel in the tables (F and G) represent hRPE65 and cRPE65 amino acid residues at the indicated positions, respectively: ex. "●●○●" in the table of 1$^{st}$ experimental set (F) indicates a triple mutant (T39R/N170K/Q497P) of hRPE65.

Plasmids expressing hRPE65 and cRPE65, and the site-directed mutants were separately transfected into 293A-LRAT cells, and the transfected cells were cultured for 48 hr. Protein expression was confirmed by Western blot analysis (relative expression levels of tested RPE65 mutants are shown in Table 2), and the same batches of total cellular proteins were used for the in vitro isomerohydrolase activity assay. For all of the hRPE65 mutants containing single, double and multiple mutations, expression levels of RPE65 were comparable (FIGS. 4A-4E), whereas the two single point mutants N170K and K297G exhibited 1.6-fold and 1.7-fold higher enzymatic activity than that of wt hRPE65, respectively, after normalization by total RPE65 expression levels (FIGS. 4F and 4G). Furthermore, the tested double, triple, or multiple mutants with N170K (or K297G) in each experimental sets did not further enhance catalytic activity of RPE65. These results suggest that mutations of N170K and K297G in hRPE65 may be important for increasing its enzymatic activity.

TABLE 2

Expression levels of generated RPE65 mutants.

| Mutant Name | Protein expression (% of WT ± SEM) | | | N = |
|---|---|---|---|---|
| wt hRPW65 | 100.0 | ± | | — |
| T39R | 119.2 | ± | 8.3 | 6 |
| N170K | 104.9 | ± | 3.3 | 7 |

TABLE 2-continued

Expression levels of generated RPE65 mutants.

| Mutant Name | Protein expression (% of WT ± SEM) | | | N = |
|---|---|---|---|---|
| C330T | 106.3 | ± | 6.5 | 6 |
| Q497P | 80.6 | ± | 8.4 | 6 |
| T39R/N170K | 102.3 | ± | 10.7 | 5 |
| N170K/C330T | 86.2 | ± | 8.7 | 5 |
| N170K/Q497P | 92.0 | ± | 4.4 | 5 |
| T39R/N170K/C330T | 92.1 | ± | 3.0 | 4 |
| T39R/N170K/Q497P | 87.9 | ± | 2.2 | 4 |
| T39R/N170K/C330T/Q497P | 108.9 | ± | 5.4 | 4 |
| C106Y | 89.0 | ± | 5.9 | 5 |
| K297G | 111.3 | ± | 7.1 | 7 |
| L510M | 171.0 | ± | 11.7 | 4 |
| S533A | 114.9 | ± | 9.1 | 5 |
| C106Y/K297G | 146.3 | ± | 8.2 | 3 |
| K297G/L510M | 186.1 | ± | 16.8 | 3 |
| K297G/S533A | 176.3 | ± | 12.2 | 3 |
| I220M | 99.2 | ± | 9.8 | 4 |
| N170K/I220M | 78.7 | ± | 2.4 | 3 |
| T39R/N170K/I220M | 103.3 | ± | 0.9 | 3 |
| T39R/N170K/I220M/Q497P | 96.9 | ± | 2.8 | 4 |
| N302I | 130.4 | ± | 14.1 | 3 |
| K297G/N302I | 145.2 | ± | 8.0 | 4 |

Construction of Chimeric Human RPE65 and its Impacts on the Protein Levels and Catalytic Activity.

To further improve the catalytic activity of hRPE65, we constructed chimeric RPE65 by replacing a peptide fragment of hRPE65 with the counterpart of cRPE65 (FIG. 5A, fragments F1-F6). At 48 hr post-transfection, the cells were harvested for Western blot analyses and in vitro isomerohydrolase assays. Western blot analysis showed that the chimeric mutants except for a F1 chimera (replaced fragment 1) displayed higher protein level of RPE65 than that of wt hRPE65 and other chimeric mutants (FIGS. 5B-5C). Interestingly, F-1 and F3 chimeric mutants showed approximately 1.5-2-fold higher catalytic activity than that of wt hRPE65, whereas the F2, F4 and F5 chimeric mutants substantially decreased its catalytic activities of hRPE65. Following the normalization by RPE65 protein levels, the F1 chimeric mutant showed the catalytic activity (106.9% of wt hRPE65) comparable to that of wt hRPE65, suggesting that the enhanced catalytic activity of the F1 chimera was likely due to the increased protein level of the F1 RPE65 chimera (FIGS. 5B, 5C). It should be noted that the F3 chimera displayed higher normalized enzymatic activity than wt hRPE65 likely due to N170K mutation (152% of wt hRPE65). This is well-correlated with the result of N170K single mutation. The F1 fragment of cRPE65 comprises residues at positions 2, 3, and 26 which are different from corresponding residues in hRPE65 (S2Y, I3S, and L26V).

Generation of Super-Isomerohydrolase (sIMH) by Combination of Highly Active Mutants.

Figures 6A, 6B:
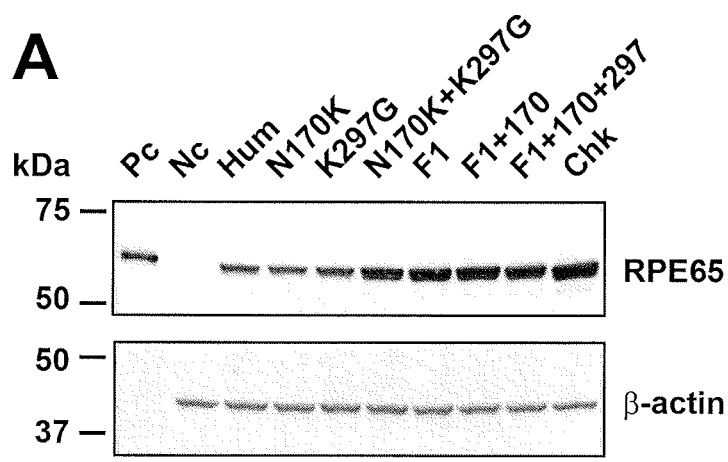
FIGS. 6A-6B show: Impacts of the site-directed mutations and fragment replacement with those of cRPE65 on protein levels and enzymatic activities of hRPE65. The identified site-directed mutants in this study (N170K and K297G) and the F1 chimera were combined to produce the mutant sIMH (F1/N170K/K297G). The identified point mutants and F1 chimera of RPE65 were expressed in 293A-LRAT cells. Cells were harvested 48 hr after the transfection, and protein levels of RPE65 were confirmed by Western blot analyses (A). Enzymatic activities were measured by in vitro isomerohydrolase assay and quantified by generated 11-[$^3$H]-cis retinol (B). Isomerohydrolase activities were quantified by generated 11-[$^3$H]-cis retinol (picomole/hr) and presented as % of wt hRPE65 activity (mean±SEM, n=3).

Combinations were made of three highly active mutants found from the series of site-directed point mutants and the chimeric mutant studies. As noted above, two single mutants (N170K and K297G) showed significantly higher catalytic activity than that of wt hRPE65 (FIG. 6B), even though their expression levels were similar to that of wt hRPE65 (FIG. 6A). As shown in FIG. 6, a double mutant (N170K/K297G) of hRPE65 demonstrated enzymatic activity 3.2-fold higher than that of wt hRPE65. In addition, a combination of the F1 chimera (having three substitutions) with the N170K mutations showed even higher (2.2-fold) protein levels and catalytic activity than that of N170K single mutant. After combining all of these mutations (S2Y/I3S/L26V/N170K/

K297G) into a single mutant, (sIMH), the catalytic activity of the mutant was found to be 4.4-fold of that of wt hRPE65, which is comparable to the activity of wt cRPE65 (5.8-fold in the same assay, FIG. 6B).

Alternate Mutants.

As shown in Table 3, certain mutations based on differences between hRPE65 and cRPE65, e.g., at positions 220 and 302, either did not improve activity, diminished activity, or diminished the improvement induced by mutations at positions 170 and 297.

TABLE 3

Isomerohydrolase activities of I220M and N302I mutant series of hRPE65.

| Mutant Name | Normalized activity (% of WT ± SEM) | | |
|---|---|---|---|
| wt hRPE65 | 100 | | |
| I220M | 62.0 | ± | 11.0 |
| N170K/I220M | 31.1 | ± | 7.8 |
| T39R/N170K/I220M | 109.7 | ± | 4.2 |
| T39R/N170K/I220M/Q497P | 108.6 | ± | 10.4 |
| N302I | 124.8 | ± | 13.3 |
| N302/K297G | 107.7 | ± | 6.9 |

Two point mutations in particular, N170K and K297G, substantially increased enzymatic activity of hRPE65. The mutant that includes both of these mutations (N170K/K297G) showed a further enhanced catalytic activity (3.2-fold of wt RPE65) of hRPE65. Furthermore, the activity of this double mutant was further enhanced by the replacement of the F1 fragment from cRPE65 ($1^{Met}$-$33^{Arg}$; containing 3 divergent residues: Y at position 2, S at position 3, and V at position 26). As a result, the catalytic activity of this super-isomerohydrolase mutant (sIMH; F1/N170K/K297G) was approximately 4.4-fold of that of wt hRPE65 under the same experimental condition, and it was contributed by 1.9-fold higher catalytic activity plus 2.3-fold higher protein level. Production of 11 cROL by sIMH was near the level of wt cRPE65 (5.8-fold of wt hRPE65).

Figure 7A:
FIGS. 7A-7C show: Analyses of catalytic efficiencies on wt hRPE65 and sIMH. Adenoviruses expressing hRPE65 and sIMH were prepared. Wt hRPE65 and sIMH were separately expressed in 293A (without LRAT) cells for 24 hr at MOI 100 and its expressions were evaluated by Western blot analysis (A). Various concentrations of substrate in liposome with total cellular protein lysates (125 µg) were applied in in vitro enzyme assays and $K_m$ and $V_{max}$ of wt hRPE65 (B) and sIMH (C) were calculated through Michaelis-Menten plot of 11cROL generation, respectively.
Figure 7B:
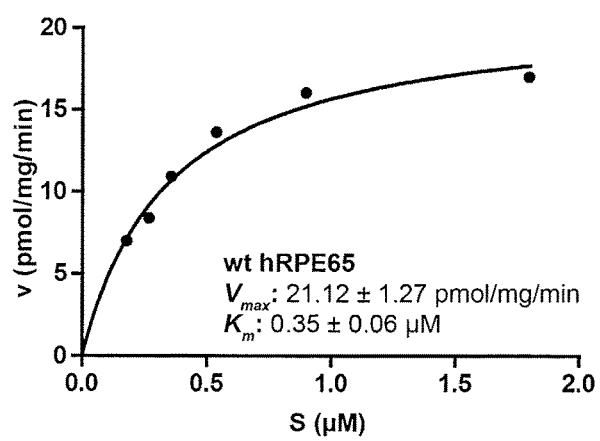
Figure 7C:
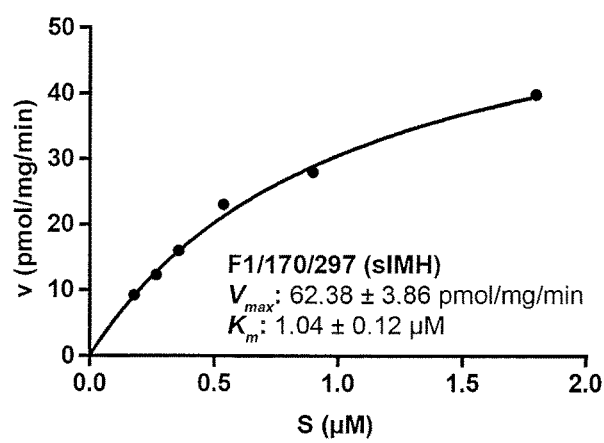

As further confirmation of enhanced enzymatic activity of sIMH, we evaluated catalytic efficiencies of wt hRPE65 and sIMH (FIG. 7). Calculated $K_m$ and $V_{max}$ suggested that higher $V_{max}$ of sIMH mainly contributes to its higher enzymatic activity (FIG. 7C).

Figures 8A, 8B, 8C:
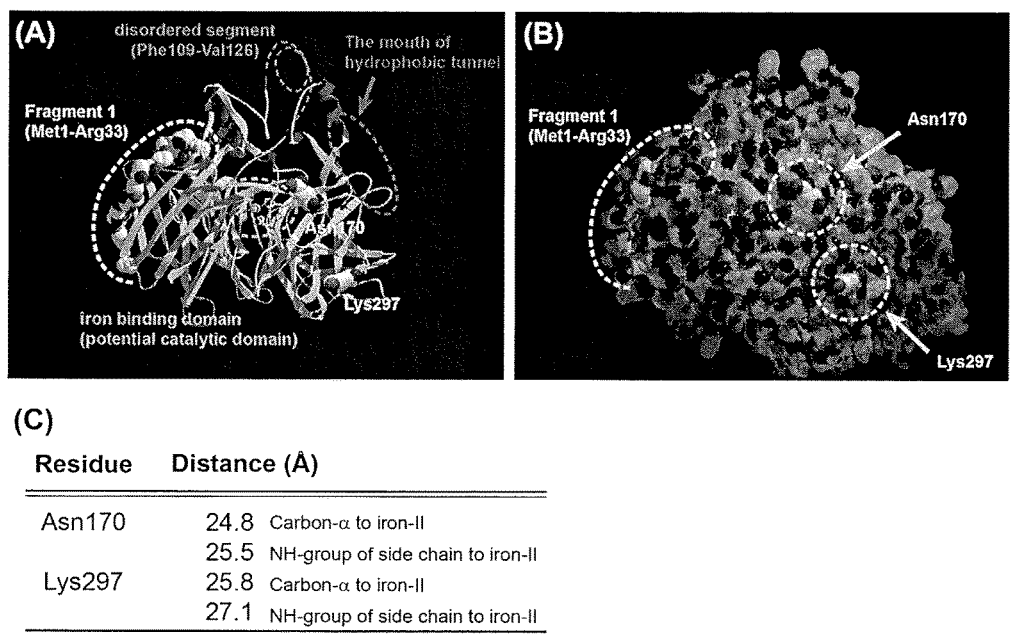
FIGS. 8A-8C show: Locations of Asn170 and Lys297, and the F1 fragment in an RPE65 3D structure model. The locations of two identified key residues and the F1 fragment are shown in the 3D model based on the crystal structure of bovine RPE65 (PDB accession: 3FSN). The iron binding site, within the catalytic domain, is indicated by an orange dotted circle. The disordered segment (Phe109-Val126), which contains a palmitylated Cys residue (Cys112), is shown by a pink dotted line. The entrance of the hydrophobic tunnel containing active site is indicated by a red dotted-circle. The location of the F1 fragment is indicated by the yellow dotted line. Both Asn170 and Lys297 residues are located on the surface of the protein (A and B) and more than 20 Å distant from iron-II in the potential catalytic domain (C).

To understand the potential contribution of the identified key residues to higher catalytic activity of cRPE65, we analyzed the 3D structure of bovine RPE65 (PDB accession: 3FSN) by a SwissPDB Viewer version 4.01 (/www.expasy.org/spdbv/) and displayed the results by a POV-Ray version 3.61 (www.povray.org/). In the 3D model, both Asn170 and Lys297 residues are localized on the surface of RPE65 molecule (FIGS. 8A, B) and distant to the co-factor iron in the RPE65 catalytic site (FIG. 8C), suggesting that these two residues are unlikely to directly participate in the catalysis of the substrate. Without wishing to be bound by theory, we speculate that these residue substitutions might improve RPE65 membrane association, e.g., for more efficient substrate intake and/or product (11cROL) release. Alternatively, these two residues might contribute to proper folding of RPE65 to achieve its active conformation upon association with the membrane. Interestingly, the F1 chimera (substituted at positions 2, 3, and 26) also revealed a significant improvement of the catalytic activity of hRPE65 due to increased protein levels of RPE65. Unlike other two residue substitutions, the F1 chimera in which only the F1 fragment is replaced with that of cRPE65 showed catalytic activity similar to that of wt hRPE65 after normalization by RPE65 protein level. The F1 fragment contains 33 amino acids and only 3 residues that differ between hRPE65 and cRPE65. These residues in the F1 fragment might contribute to proper folding to enhance protein stability of the hRPE65 mutant. Another possibility is the contribution of the nucleotide sequence difference. Among the 99 base pairs encoding the 33 amino acids in the F1 fragment, there are 19 different nucleotides between hRPE65 and cRPE65. These nucleotide substitutions might improve the stability of the hRPE65 mRNA or contribute to more efficient codon usage, leading to higher levels of expression.

As can be seen from the above, the present work generated, in at least one embodiment, a highly active hRPE65 mutant, (herein designated as super-isomerohydrolase (sIMH)), by substituting wild type 5 residues (at positions 2, 3, 26, 170, and 297) with residues of the corresponding amino acid positions of cRPE65. This sIMH displayed higher catalytic activity (4.4-fold higher than wt RPE65) after normalization by the total cellular protein levels. In one embodiment, this sIMH mutant can be used in RPE65 gene replacement therapy for more effective treatment of retinal dystrophies in human subjects. Other substitutions which may be made to form other mutants of the presently disclosed inventive concepts, based on other mammalian RPE65 sequences (including, but not limited to, other mammalian RPE65 sequences described herein), include, but are not limited to, those shown in FIG. 9. For example, in one or more non-limiting embodiments, at position 2, Phe or His could be used as the substituted amino acid instead of Tyr, at position 3, Thr or Cys could be used as the substituted amino acid instead of Ser, at position 26, Ala or Ile could be used as the substituted amino acid instead of Val, at position 170, Arg or His could be used as the substituted amino acid instead of Lys, and at position 297, Ala could be used as the substituted amino acid instead of Gly. For example, any of the mutants formed based on SEQ ID NO:1 can also be made in any of the mammalian RPE65 sequences SEQ ID NO:5, SEQ ID NO:7, SEQ ID NO:9, SEQ ID NO:11, SEQ ID NO:13, SEQ ID NO:15, or SEQ ID NO:17.

In vitro activity assay of indicated mutants were performed as described herein and isomerohydrolase activities were expressed as relative activity following the normalization of RPE65 levels (% of wt hRPE65 activity, mean±SEM, n=3).

While the presently disclosed inventive concepts have been described herein in connection with certain embodiments so that aspects thereof may be more fully understood and appreciated, it is not intended that the presently disclosed inventive concepts be limited to these particular embodiments. On the contrary, it is intended that all alternatives, modifications and equivalents are included within the scope of the presently disclosed inventive concepts as defined herein. Thus the examples described above, which include particular embodiments, will serve to illustrate the practice of the presently disclosed inventive concepts, it being understood that the particulars shown are by way of example and for purposes of illustrative discussion of particular embodiments of the presently disclosed inventive concepts only and are presented in the cause of providing what is believed to be the most useful and readily understood description of procedures as well as of the principles and conceptual aspects of the inventive concepts. Changes may be made in the formulation of the various compositions described herein, the methods described herein or in the steps or the sequence of steps of the methods described herein without departing from the spirit and scope of the presently disclosed inventive concepts. Further, while various embodiments of the presently disclosed inventive concepts have been described in claims herein below, it is not intended that the presently disclosed inventive concepts be limited to these particular claims.

What is claimed is:

1. A nucleic acid encoding an RPE65 protein or portion thereof comprising an amino acid sequence having at least 95% identity to SEQ ID NO:1 and comprising amino acid substitutions in positions 170 and 297, and in at least one of positions 3 and 26, of SEQ ID NO:1; said RPE65 protein or portion thereof having isomerohydrolase activity.

2. The nucleic acid of claim 1, wherein the amino acid substitution in position 170 is selected from K, R, and H, and the amino acid substitution in position 297 is selected from G and A.

3. The nucleic acid of claim 1, wherein the RPE65 protein or portion thereof further comprises an amino acid substitution in position 2 of SEQ ID NO:1.

4. The nucleic acid of claim 3, wherein the amino acid substitution in position 2 is selected from Y, F, and H.

5. The nucleic acid of claim 1, wherein said RPE65 protein or portion thereof further comprises amino acid substitutions in both of positions 3 and 26.

6. The nucleic acid of claim 1, wherein the amino acid substitution in position 3 is selected from S, T, and C; and the amino acid substitution in position 26 is selected from V, A, and I.

7. The nucleic acid of claim 1, wherein the RPE65 protein or portion thereof comprises amino acid substitutions in positions 2 and 3 or in positions 2 and 26 of SEQ ID NO:1.

8. The nucleic acid of claim 7, wherein the amino acid substitution in position 2 is selected from Y, F, and H; the amino acid substitution in position 3 is selected from S, T, and C; and the amino acid substitution in position 26 is selected from V, A, and I.

9. The nucleic acid of claim 1, wherein said RPE65 protein or portion thereof comprises amino acid substitutions in all of positions 2, 3, and 26 of SEQ ID NO:1.

10. The nucleic acid of claim 9, wherein the amino acid substitution in position 2 is selected from Y, F, and H; the amino acid substitution in position 3 is selected from S, T, and C; and the amino acid substitution in position 26 is selected from V, A, and I.

11. The nucleic acid of claim 1, encoding at least one amino acid substitution or combination of amino acid substitutions selected from the group consisting of T39R, C330T, Q497P, C106Y, L510M, S533A, I220M, and N302I.

12. The nucleic acid of claim 1, encoding at least one amino acid substitution or combination of amino acid substitutions selected from the group consisting of T39R, C330T, Q497P, C106Y, L510M, S533A, I220M, N302I, T39R/N170K, N170K/C330T, N170K/Q497P, C106Y/K297G, K297G/L510M, K297G/S533A, N170K/I220M, K297G/N302I, C106Y/N170K, S2Y/I3S/L26V, T39R/N170K/C330T, T39R/N170K/Q497P, T39R/N170K/I220M, C330T/Q497P/L510M, T39R/N170K/C330T/Q497P, T39R/N170K/I220M/Q497P, S2Y/I3S/L26V/N170K, and S2Y/I3S/L26V/N170K/K297G.

13. The nucleic acid of claim 1, encoding at least one amino acid substitution or combination of amino acid substitutions is selected from the group consisting of T39R, S533A, T39R/N170K, N170K/Q497P, K297G/L510M, K297G/S533A, C106Y/N170K, S2Y/I3S/L26V, T39R/N170K/Q497P, S2Y/I3S/L26V/N170K, and S2Y/I3S/L26V/N170K/K297G.

14. The nucleic acid of claim 1, wherein the amino acid substitution in position 170 is K, and the amino acid substitution in position 297 is G.

15. The nucleic acid of claim 14, wherein said RPE65 protein or portion thereof comprises amino acid substitutions in positions 2, 3, and 26 of SEQ ID NO:1.

16. The nucleic acid of claim 15, wherein the amino acid substitution in position 2 is Y; the amino acid substitution in position 3 is S; and the amino acid substitution in position 26 is V.

17. A viral vector comprising the nucleic acid of claim 1, wherein the viral vector is selected from the group consisting of adenovirus and adeno-associated virus (AAV).

18. The viral vector of claim 17, comprising an AAV vector comprising an AAV capsid sequence.

19. The viral vector of claim 18, wherein said AAV capsid sequence comprises a VP1, VP2 and/or VP3 capsid sequence having at least 90% identity to the VP1, VP2 and/or VP3 sequences of AAV1, AAV2, AAV3, AAV4, AAV5, AAV6, AAV7, AAV8, AAV9, AAV10, AAV11, Rh10, Rh74 or AAV-2i8.

20. The viral vector of claim 18, comprising a promoter or enhancer sequence operatively-linked to said nucleic acid, a stop codon or a poly-A sequence located 3' of said nucleic acid, and/or one or more AAV inverted terminal repeat (ITR) sequences.

21. The viral vector of claim 20, wherein said promoter or enhancer sequence comprises a RPE65 promoter sequence or a CMV enhancer/chicken β-actin promoter sequence.

22. The viral vector of claim 20, wherein the one or more AAV ITR sequences comprises an ITR sequence selected from the group consisting of AAV1, AAV2, AAV3, AAV4, AAV5, AAV6, AAV7, AAV8, AAV9, AAV10, AAV11, Rh10, Rh74 or AAV-2i8 AAV serotypes, and mixtures of ITR sequences therefrom.

23. A gene therapy method of treating a condition related to retinal degeneration in a mammalian subject in need of such treatment, said method comprising: administering to said subject a therapeutically-effective amount of the viral vector of claim 17, wherein the RPE65 protein or portion thereof encoded by the nucleic acid is expressed in vivo in retinal cells of said subject and has isomerohydrolase activity.

* * * * *